United States Patent [19]

Domagala et al.

[11] Patent Number: 5,097,032
[45] Date of Patent: Mar. 17, 1992

[54] ANTIBACTERIAL AGENTS - II

[75] Inventors: John M. Domagala, Canton; Thomas F. Mich, Ann Arbor; Joseph P. Sanchez, Canton, all of Mich.

[73] Assignee: Warner-Lambert Company, Morris Plains, N.J.

[21] Appl. No.: 537,548

[22] Filed: Jun. 13, 1990

Related U.S. Application Data

[60] Division of Ser. No. 297,354, Jan. 17, 1989, abandoned, which is a division of Ser. No. 920,536, Oct. 20, 1986, Pat. No. 4,822,801, which is a continuation-in-part of Ser. No. 770,897, Aug. 30, 1985, abandoned, which is a continuation-in-part of Ser. No. 633,153, Jul. 20, 1984, abandoned.

[30] Foreign Application Priority Data

Feb. 7, 1985 [IE] Ireland ............................. 1666/85

[51] Int. Cl.$^5$ ................. C07D 471/04; C07D 215/233
[52] U.S. Cl. ...................................... 546/156; 546/123
[58] Field of Search ............................. 546/123, 156

[56] References Cited

U.S. PATENT DOCUMENTS 4,571,396 2/1986 Hutt et al. ...................... 546/123 X
4,665,079 5/1987 Culbertson et al. ............. 546/123 X

FOREIGN PATENT DOCUMENTS 0047005  3/1982  European Pat. Off. .
57-149286  9/1982  Japan .
58-174367A 10/1983  Japan .

OTHER PUBLICATIONS

*J. Med. Chem.*, 23, 1358–1363 (1980), Koga, et al..
*Antimicr. Agents and Chemotherapy*, 6, 124–135 (1974), Heifetz, et al.
*Eur. J. Med. Chem.–Chimica Therapeutica*, 12, 27–29 (1977), Rufer, et al.
*J. Org. Chem.*, 46, 2757–2764 (1981), Overberger, et al.
*J. Org. Chem.*, 26, 1519–1524 (1961), Wu et al.
*J. Org. Chem.*, 26, 4955–4959 (1961), Wu et al.

*Primary Examiner*—Richard L. Raymond
*Attorney, Agent, or Firm*—Elizabeth M. Anderson

[57] ABSTRACT

Novel naphthyridine-, quinoline- and benzoxazinecarboxylic acids as antibacterial agents are described as well as methods for their manufacture, formulation, and use in treating bacterial infections including the description of certain novel intermediates used in the manufacture of the antibacterial agents.

5 Claims, No Drawings

ANTIBACTERIAL AGENTS - II

CROSS-REFERENCE TO RELATED APPLICATION

This is a divisional of U.S. application Ser. No. 297,354 filed Jan. 17, 1989, now abandoned which is a divisional of U.S. application Ser. No. 920,536 filed Oct. 20, 1986, now U.S. Pat. No. 4,822,801, which is a continuation-in-part of U.S. application Ser. No. 770,897 filed Aug. 30, 1985, now abandoned, which is a continuation-in-part of U.S. application Ser. No. 633,153 filed Jul. 20, 1984, now abandoned, and which claims priority to Irish Application 1666/85 filed Feb. 7, 1985.

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3-carboxylic acids having the general formula:

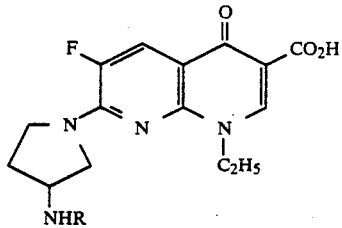

The compounds are disclosed to have antibacterial activity.

The Journal of Medicinal Chemistry, 23, 1358 (1980) discloses certain substituted quinoline-3-carboxylic acids having the structural formula

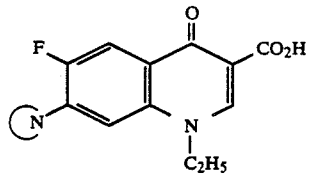

wherein

may be pyrrolidinyl. See also U.S. Pat. No. 4,146,719. The compounds are disclosed to have antibacterial activity.

European Patent Application 81 10 6747, Publication Number 047,005, published Mar. 10, 1982, discloses certain benzoxazine derivatives having the structural formula

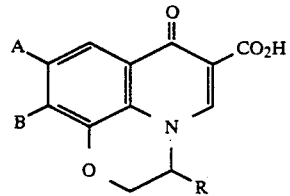

wherein A is halogen and B may be a cyclic amine substituent such as pyrrolidine, or piperidine.

Certain 7-heterocyclic substituted 1,8-naphthyridines are disclosed in Eur. J. Med. Chem.-Chimica Therapeutica, 29, 27 (1977). U.S. Pat. Nos. 3,753,993 and 3,907,808 disclose certain 7-pyridylquinolones.

The references teach that these compounds possess antibacterial activity.

SUMMARY OF THE INVENTION

The invention in a first generic chemical compound aspect are compounds having the structural formula I and II

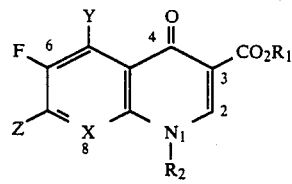

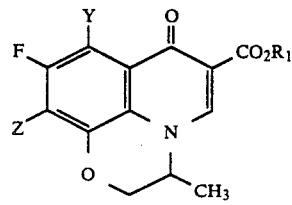

wherein Z is

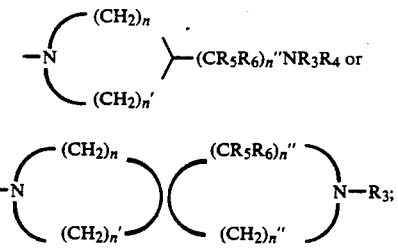

Y is $NH_2$, NHR, NRR', OR, or OH wherein R and R' are each independently an alkyl of from one to six carbon atoms or a cycloalkyl of from three to six carbon atoms; X is CH, CF, CCl, CBr, COR, COH, $CCF_3$, or N; n is 1, 2, 3, or 4; n' is 1, 2, 3, or 4 wherein n+n' is a total of 2, 3, 4, or 5, and n" is 0, 1, or 2; $R_1$ is hydrogen, alkyl having from one to six carbon atoms or a cation; $R_2$ is alkyl having from one to four carbon atoms, vinyl, haloalkyl, or hydroxyalkyl having from two to four carbon atoms, or cycloalkyl having three to six carbon atoms; $R_3$ is hydrogen, alkyl having from one to four carbon atoms or cycloalkyl having three to six carbon atoms; $R_4$ is hydrogen, alkyl from one to four carbon atoms, hydroxyalkyl having two to four carbon atoms, trifluoroethyl or R₇CO— wherein R₇ is alkyl having from one to four carbon atoms, or alkoxy having from one to four carbon atoms; R₅ is hydrogen, or alkyl having from one to three carbon atoms; R₆ is hydrogen or alkyl having from one to three carbon atoms; and the pharmaceutically acceptable acid addition or base salts thereof.

The preferred compounds of this invention are those wherein Z is

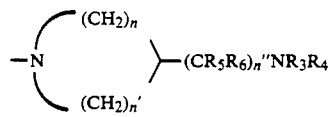

Also preferred compounds of this invention are those wherein Z is

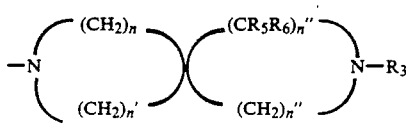

Other preferred compounds of this invention are those wherein $R_1$ is hydrogen or a pharmaceutically acceptable base salt such as a metal or amine salt.

Other preferred compounds of this invention are those wherein $R_2$ is ethyl, vinyl, 2-fluoroethyl, or cyclopropyl.

The most preferred compounds are those wherein X is N, CF, or CCl, Z is

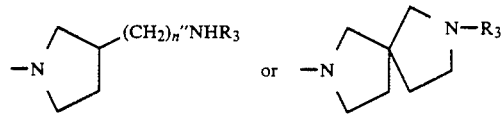

$R_1$ is hydrogen, $R_2$ is ethyl, vinyl, 2-fluoroethyl or cyclopropyl; n″ is 0 or 1 and $R_3$ is hydrogen, methyl, ethyl, 1- or 2-propyl, Y is NH₂ or a pharmaceutically acceptable acid addition or base salt thereof.

Particularly preferred species of the invention are the compounds having the names:

8-amino-9-fluoro-3-methyl-10[(3-cyclopropylaminomethyl)-1-pyrrolidinyl]-7-oxo-2,3-dihydro-7H-pyrido[1,2,3-de][1,4]benzoxazine-6-carboxylic acid;
8-amino-9-fluoro-3-methyl-10-(3-amino-1-pyrrolidinyl)-7-oxo-2,3-dihydro-7H-pyrido[1,2,3-de][1,4]benzoxazine-6-carboxylic acid hydrochloride;
8-amino-9-fluoro-3-methyl-10-[3-(aminomethyl)-1-pyrrolidinyl]-7-oxo-2,3-dihydro-7H-pyrido[1,2,3-de][1,4-]benzoxazine-6-carboxylic acid;
8-amino-9-fluoro-3-methyl-10-[3-[(propylamino)methyl]-1-pyrrolidinyl]-7-oxo-2,3-dihydro-7H-pyrido[1,2,3-de][1,4]benzoxazine-6-carboxylic acid;
8-amino-9-fluoro-3-methyl-10-[3-[(2-hydroxyethyl)amino)methyl]-1-pyrrolidinyl]-7-oxo-2,3-dihydro-7H-pyrido[1,2,3-de][1,4]benzoxazine-6-carboxylic acid;
8-amino-9-fluoro-3-methyl-10-[3-[(2-propylamino)methyl]-1-pyrrolidinyl]-7-oxo-2,3-dihydro-7H-pyrido[1,2,3-de][1,4]benzoxazine-6-carboxylic acid;
8-amino-9-fluoro-3-methyl-10-[3-[(2,2,2-trifluoroethyl)amino]methyl]-1-pyrrolidinyl]-7-oxo-2,3-dihydro-7H-pyrido[1,2,3-de][1,4]benzoxazine-6-carboxylic acid;
8-amino-9-fluoro-3-methyl-10-[3-[(ethylamino)methyl]-1-pyrrolidinyl]7oxo-2,3-dihydro-7H-pyrido[1,2,3-de][1,4]benzoxazine-6-carboxylic acid;
8-amino-9-fluoro-3-methyl-10-[2,7-diazaspiro[4.4]non-2-yl]-7-oxo-2,3-dihydro-7H-pyrido[1,2,3-de][1,4]benzoxazine-6-carboxylic acid;
8-amino-9-fluoro-3-methyl-10-[7-(7-methyl-2,7-diazaspiro[4.4]non-2-yl]-7-oxo-2,3-dihydro-7H-pyrido[1,2,3-de][1,4]benzoxazine-6-carboxylic acid;
8-amino-9-fluoro-3-methyl-10-[7-(7-ethyl-2,7-diazaspiro[4.4]non-2-yl]-7-oxo-2,3-dihydro-7H-pyrido[1,2,3-de][1,4]benzoxazine-6-carboxylic acid;
1-ethyl-5-amino-6,8-difluoro-7-(3-amino-1-pyrrolidinyl)-4-oxo-1,4-dihydroquinoline-3-carboxylic acid hydrochloride;
1-ethyl-5-amino-6,8-difluoro-7-[3-(ethylamino)methyl-1-pyrrolidinyl)]-4-oxo-1,4-dihydroquinoline-3-carboxylic acid;
1-ethyl-5-amino-6,8-difluoro-7-[3-(aminomethyl)-1-pyrrolidinyl]-4-oxo-1,4-dihydroquinoline-3-carboxylic acid;
1-ethyl-5-amino-6,8-difluoro-7-[3-(propylaminomethyl)-1-pyrrolidinyl]-4-oxo-1,4-dihydroquinoline-3-carboxylic acid;
1-ethyl-5-amino-6,8-difluoro-7-[3-(2-propylaminomethyl)-1-pyrrolidinyl]-4-oxo-1,4-dihydroquinoline-3-carboxylic acid;
1-ethyl-5-amino-6,8-difluoro-7-[3-(cyclopropylaminomethyl)-1-pyrrolidinyl]-4-oxo-1,4-dihydroquinoline-3-carboxylic acid;
1-ethyl-5-amino-6,8-difluoro-7-[2,7-diazaspiro[4.4]non-2-yl]-4-oxo-1,4-dihydroquinoline-3-carboxylic acid;
1-ethyl-5-amino-6,8-difluoro-7-[7-(7-methyl-2,7-diazaspiro[4.4]non-2-yl]-4-oxo-1,4-dihydroquinoline-3-carboxylic acid;
1-ethyl-5-amino-6,8-difluoro-7-[7-(7-ethyl-2,7-diazaspiro[4.4]non-2-yl]-4-oxo-1,4-dihydroquinoline-3-carboxylic acid;
1-ethyl-5-amino-6,8-difluoro-7-[3-[[(2-hydroxyethyl)amino]methyl]-1-pyrrolidinyl]-4-oxo-1,4-dihydroquinoline-3-carboxylic acid;
1-ethyl-5-amino-6,8-difluoro-7-[3-[[(2,2,2-trifluoroethyl)amino]methyl]-1-pyrrolidinyl]-4-oxo-1,4-dihydroquinoline-3-carboxylic acid;
5-amino-7-(3-amino-1-pyrrolidinyl)-1-ethyl-6-fluoro-1,4-dihydro-4-oxo-1,8-naphthyridine-3-carboxylic acid;
5-amino-7-(3-amino-1-pyrrolidinyl)-8-chloro-1-cyclopropyl-6-fluoro-1,4-dihydro-4-oxo-3-quinolinecarboxylic acid;
5-amino-8-chloro-1-cyclopropyl-6-fluoro-1,4-dihydro-7-[3-[(methylamino)methyl]-1-pyrollidinyl]-4-oxo-3-quinolinecarboxylic acid;
5-amino-7-(3-amino-1-pyrrolidinyl)-8-bromo-1-cyclopropyl-6-fluoro-1,4-dihydro-4-oxo-3-quinolinecarboxylic acid; and
5-amino-7-(3-amino-1-pyrrolidinyl)-1-cyclopropyl-6,8-difluoro-1,4-dihydro-4-oxo-3-quinolinecarboxylic acid.

The following process for preparing compounds of the formula

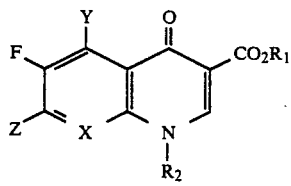

or

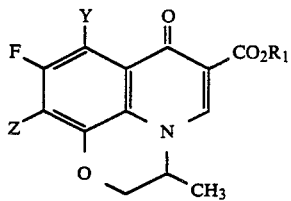

wherein $R_1$, $R_2$, X, and Z are as defined for formula I which comprises reacting a compound having the following structural formula

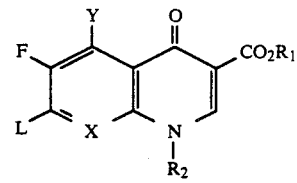

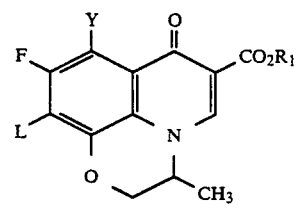

with an amine corresponding to the group Z wherein Z is the compound having the structural formula

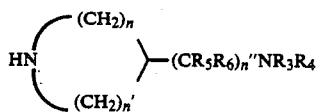

or

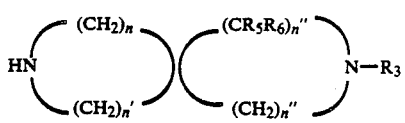

wherein all of the above terms are as defined in formulae I and II and L is a leaving group which is preferably fluorine or chlorine.

This invention also includes novel intermediates. In a second generic chemical aspect are compounds having the structural formula VII

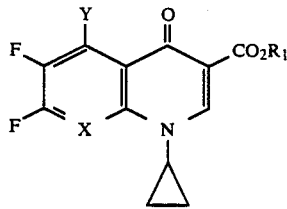

wherein X is CH, N, CF, CCl, CBr, CCF$_3$, COH, or COR; Y is NH$_2$, NHR, NRR', OR or OH wherein R and R" are each independently an alkyl of from one to six carbon atoms or a cycloalkyl of from three to six carbon atoms; $R_1$ is as defined above and the pharmaceutically acceptable acid addition or base salts thereof. The preferred compounds are those wherein X is CCl, CBr, or CF and Y is NH$_2$, NHR, or NRR'.

Particularly preferred species of the invention are compounds having the names:

5-amino-8-chloro-1-cyclopropyl-6,7-difluoro-1,4-dihydro-4-oxo-3-quinolinecarboxylic acid;

5-amino-8-bromo-1-cyclopropyl-6,7-difluoro-1,4-dihydro-4-oxo-3-quinolinecarboxylic acid; and 5-amino-1-cyclopropyl-6,7,8-trifluoro-1,4-dihydro-4-oxo-3-quinolinecarboxylic acid.

The invention also includes a pharmaceutical composition which comprises an antibacterially effective amount of a compound having structural formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the invention having the structural formula III or IIIa may be readily prepared by treating a corresponding compound having the structural formula IV or V with the desired cyclic amine VIa or VIb. For purposes of this reaction, the alkylamine substituent of compound VIa or VIb may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between compound IV or V and compound VIa or VIb if desired, by procedures known to those skilled in the art. For example, the ethoxycarbonyl group may be removed by acid or base hydrolysis and the trityl group may be removed by hydrogenolysis.

The reaction between the compound of structural formula IV or V and a suitably protected compound of formula VIa or VIb, may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of formula VI may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group $R_4$ may be accomplished either before or after isolating the product, III. Alternatively, the protecting group $R_4$ need not be removed.

Some of the starting compounds having structural formulae IV and V are known in the art or, if new, may be prepared from known starting materials by standard procedures or by variations thereof. Thus the following compounds are disclosed in the noted references:

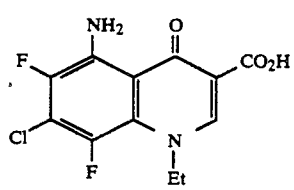

J5 8174 367A

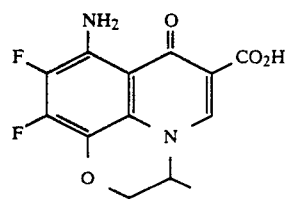

J5 7149 286

Other starting compounds having structural formula IV wherein Y is NRR' and R and/or R' are not hydrogen may be prepared from the known 5-amino quinolines or naphthyridines by an alkylation sequence shown below wherein L is a leaving group as previously defined.

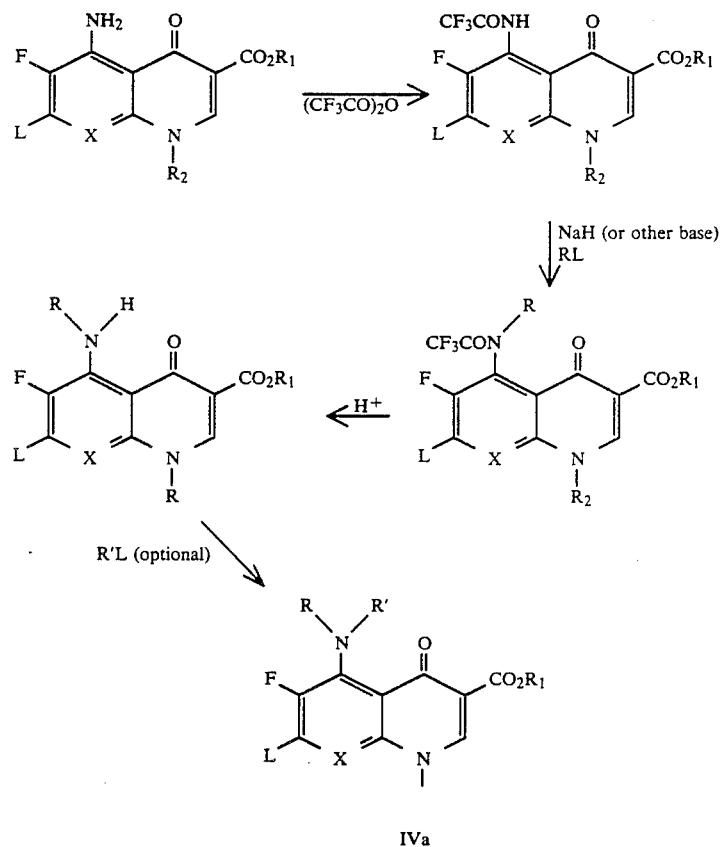

IVa

The 5-amino group is preferably acylated by trifluoroacetic acid anhydride although other acyl moieties may be employed. The alkylation of R proceeds with the presence of sodium hydride or other nonnucleophilic bases. Removal of the acyl activating group is accomplished with acid or base hydrolysis such as 2N hydrochloric acid in acetic acid. A second alkylation, if desired, with R'L, again in the presence of base such as, for example, potassium carbonate provides compounds of formula IV where both R and R' are not hydrogen.

Alternatively, the 5-alkylamino compounds of formula II may be prepared from the nitro or amino acids IV through reductive amination procedures as illustrated in the following scheme.

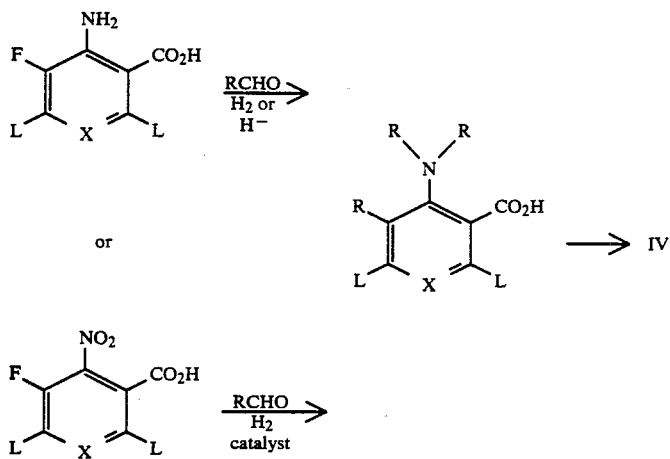

Using appropriate control of the aldehyde (RCHO) equivalents mono and disubstituted amines may be obtained. The substituted amino acids may be converted to the desired compounds of formula II by methods described in the references cited in the Background of the Invention.

The compounds of formula IV wherein Y is OR may be prepared from the polysubstituted acids or esters by displacement of an ortho leaving group with OR as shown:

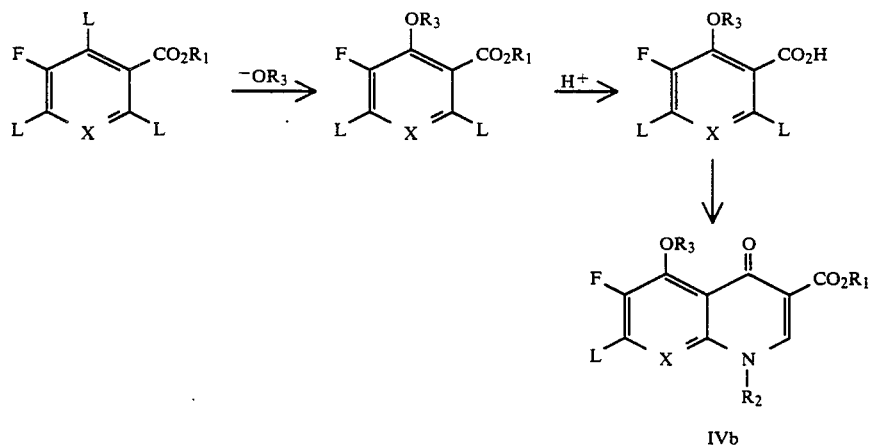

Other compounds of formula IV wherein X is CH, CCl, CBr, COR, COH, CCF$_3$ or N are made by the sequence shown below according to the general methods in the references cited in the background of the invention.

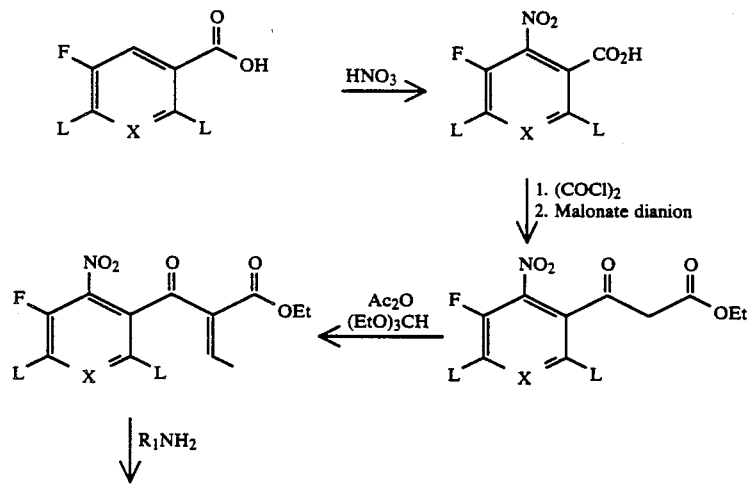

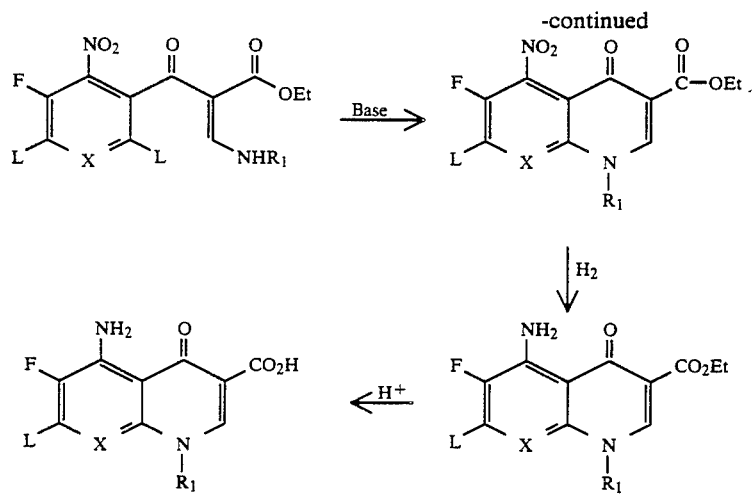

The general pathway to the compounds of formula IV is illustrated with 2-nitro-3,4,5,6-tetrafluorobenzoyl chloride. This starting material is treated with n-butyl lithium and malonic half acid ester to form 2-nitro-3,4,5,6-tetrafluoro-β-oxo-benzene propanoic acid ethyl ester. This product can be converted to 5-nitro-1-cyclopropyl-6,7,8-trifluoro-1,4-dihydro-4-oxo-quinoline-3-carboxylic acid ethyl ester by a three step reaction. The starting material is first treated with triethylorthoformate and subsequently with cyclopropyl amine in t-butyl alcohol. The product is ring closed with potassium t-butoxide to form 5-nitro-1-cyclopropyl-6,7,8-trifluoro-1,4-dihydro-4-oxoquinoline-3-carboxylic acid ethyl ester. This product is hydrogenated to form the corresponding 5-amino compound. This is then hydrolyzed to form 1-cyclopropyl-5-amino-6,7,8-trifluoro-1,4-dihydro-4-oxo-3-quinoline carboxylic acid. Alternatively compounds of the formula IV may be prepared by a series of reactions illustrated with 3,4,5,6-tetrafluoroanthranilic acid. The acid is reacted with acetic anhydride and acetic acid to form 2-acetylamino-3,4,5,6-tetrafluorobenzoic acid. This compound is reacted with oxalyl chloride and dichloromethane in the presence of N,N-dimethylformamide catalyst to form 2-acetylamino-3,4,5,6-tetrafluorobenzoyl chloride. This product is treated with n-butyl lithium and malonic half acid ester to form 2-acetylamino-3,4,5,6-tetrafluoro-β-oxobenzenepropanoic acid ethyl ester.

This product can be converted to 5-acetylamino-1-cyclopropyl-6,7,8-trifluoro-1,4-dihydro-4-oxoquinoline-3-carboxylic acid ethyl ester by a three step reaction. The 2-acetylamino-3,4,5,6-tetrafluoro-β-oxobenzene-propanoic acid ethylester is first treated with triethylorthoformate and acetic anhydride. After removal of the solvent the residue is treated with a solution of cyclopropylamine in t-butanol. After the reaction is complete a solution of potassium t-butoxide in t-butanol is added. The resulting product is 5-acetylamino-1-cyclopropyl-6,7,8-trifluoro-1,4-dihydro-4-oxo-quinoline-3-carboxylic acid ethyl ester. The ester is hydrolyzed to form 1-cyclopropyl-5-amino-6,7,8-trifluoro-1,4-dihydro-4-oxo-3-quinolinecarboxylic acid.

The compounds of the invention having structural formula VIa or VIb are either known compounds or they may be prepared from known starting materials by standard procedures or by variations thereof. For example, 3-pyrrolidinemethanamines having the structural formula D may be readily prepared from the known starting material methyl 5-oxo-1-(phenylmethyl)-3-pyrrolidinecarboxylate, A, [J. Org. Chem., 26, 1519 (1961)] by the following reaction sequence.

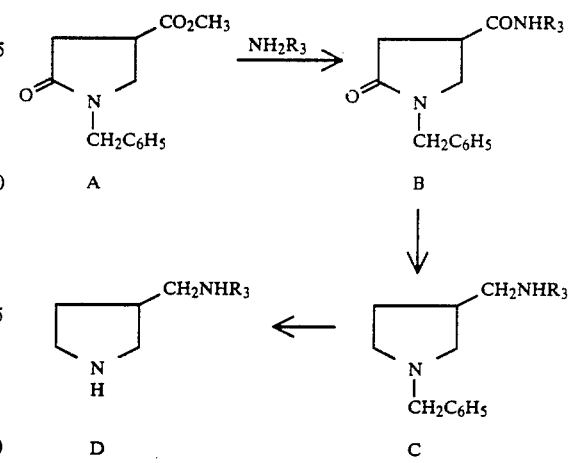

The compound wherein $R_3$ is hydrogen, namely 3-pyrrolidinemethanamine, has been reported in J. Org. Chem., 26, 4955 (1961).

Thus compound A may be converted to the corresponding amide B by treatment with $R_3NH_2$; for example, a saturated solution of ethylamine in an alkanol such as methyl alcohol may be utilized. The diamide B may next be reduced to produce the corresponding diamine C. This reduction may be carried out using lithium aluminum hydride, for example, in a convenient solvent such as tetrahydrofuran. Compound C may next be debenzylated, for example using hydrogen and 20% palladium on carbon catalyst to produce the diamine D. Alternatively, when R=H in C, the primary amine function may be protected with a group $R_4$ as defined, hereinabove. For example, the primary amine function may be acylated with an acyl halide such as acetyl chloride by well known procedures. The primary amine function of C may also be converted to a carbamate ester such as the ethyl ester by treatment with ethyl chloroformate in the presence of a strong base such as 1,8-diazabicyclo[5.4.0]undec-7-ene in a convenient solvent such as methylene chloride. The benzyl group may next be removed, for example as described above for compound C, thereby producing compound D where R is —CO₂Et, which after conversion to a compound of the type VIa or VIb may be reacted with a compound having the structural formula IV or V to thereby produce a corresponding compound having the structural formula I or Ia. The —CO₂Et group may be removed by standard procedures.

Likewise spiroamino compounds represented by structural formula VIb may be readily prepared from the known starting material 3-ethoxycarbonyl-5-oxo-3-pyrrolidineacetic acid ethyl ester [J. Org. Chem. 46, 2757 (1981)] by the following reaction sequence.

thylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, citric, oxalic, malonic, salicyclic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous soldium hydroxide, potassium carbonate, ammonia, and sodium bicarbonate solutions are suitable for this purpose. The free base forms differ from their respective salt forms somewhat in certain physical properties such as solubil-

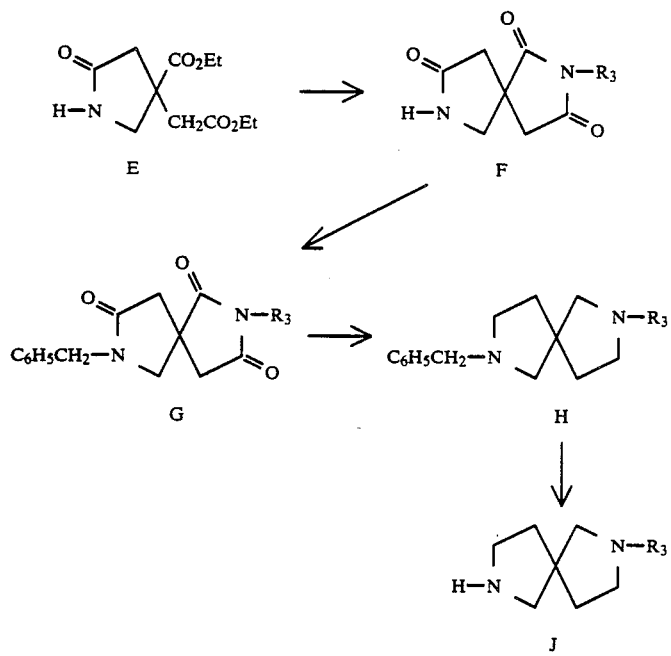

The compound 2,7-diazaspiro[4.4]nonane where R₃ is H is described in the above reference. Thus compound E may be converted to the corresponding amide F by treatment with R₃NH₂, for example, methyl amine in water followed by benzylation which may be carried out with sodium hydride and benzyl chloride to give G. Reduction to the diamine H may be accomplished with lithium aluminum hydride. Subsequent debenzylation, for example, with hydrogen and 20% palladium on carbon catalyst produces the diamine J.

The compounds of the invention display antibacterial activity when tested by the microtitration dilution method as described in Heifetz, et al, Antimicr. Agents & Chemoth., 6, 124 (1974), which is incorporated herein by reference.

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzyleity in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about six carbon atoms. Representative of such groups are methyl, ethyl, propyl, isopropyl, and the like.

The cycloalkyl groups contemplated by the invention comprise those having three to six carbon atoms such as cyclopropyl, cyclobutyl, cyclopentyl, and cyclohexyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substitutent may not be present on the α-carbon atom of the chain. Representative of such groups are β-fluoroethyl, β-chloroethyl, β,β-dichloroethyl, β-chloropropyl, β-chloro-2-propyl, -iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional asymmetric carbon atoms may be present in a substitutent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

PREPARATION OF STARTING MATERIALS

Example A

1-Ethenyl-6,7,8-trifluoro-1,8-dihydro-4-oxo-3-quinolinecarboxylic acid 6,7,8-Trifluoro-1,4-dihydro-4-oxo-3-quinolinecarboxylic acid ethyl ester was treated with dibromo ethane to afford the 1-ethenyl-6,7,8-trifluoro-1,4-dihydro-4-oxo-3-quinolinecarboxylic acid ester, mp 134–135° C. Subsequent hydrolysis with hydrochloric acid gave 1-ethenyl-6,7,8-trifluoro-1,4-dihydro-4-oxo-3-quinolinecarboxylic acid, mp 186–187° C.

Example B 6,7,8-Trifluoro-1-(2-fluoroethyl)-1,4-dihydro-4-oxo-3-quinolinecarboxylic acid In identical fashion, 6,7,8-trifluoro-1,4-dihydro-4-oxo-3-quinolinecarboxylic acid ethyl ester was converted to 6,7,8-trifluoro-1-(2-fluoroethyl)-1,4-dihydro-4-oxo-3-quinolinecarboxylic acid, mp 207–211° C.

Example C

N-Methyl-3-pyrrolidinemethanamine

N-Methyl-5-oxo-1-(phenylmethyl)-3-pyrrolidinecarboxamide

A mixture of 100 g (0.43 mole) of methyl 5-oxo-1-(phenylmethyl)-3-pyrrolidinecarboxylate [J. Org. Chem., 26, 1519 (1961)], 500 ml methanol and 100 g (3.2 mole) of methylamine was heated at 100° C. in a pressure reactor for 16 hours. The reaction mixture was cooled and the ammonia and methanol were removed under pressure. The residue was taken up in dichloromethane and washed 3×100 ml 1N sodium hydroxide. The organic layer was dried over magnesium sulfate and the solvent removed at reduced pressure to give 88.3 g of N-methyl-5-oxo-1-(phenylmethyl)-3-pyrrolidinecarboxamide as a white solid, mp 82.5–83.0° C.

| Analysis calculated for $C_{13}H_{16}N_2O_2$: | | |
|---|---|---|
| C, 67.22; | H, 6.94; | N, 12.06 |
| Found C, 66.98; | H, 6.69; | N, 12.02. |

This material was used in the next step.

N-Methyl-1-(phenylmethyl)-3-pyrrolidinemethanamine

To a suspension of 37.4 g (1.00 mole) lithium aluminum hydride in 1000 ml tetrahydrofuran, was added a solution of 88.3 g (0.380 mole) of N-methyl-5-oxo-1-(phenylmethyl)-3-pyrrolidinecarboxamide in tetrafuran dropwise under nitrogen. The reaction was then refluxed overnight. The reaction flask was cooled in an ice bath and 37.4 ml of water 37.4 ml of 15% sodium hydroxide and 112.2 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 68.7 g of N-methyl-1-(phenylmethyl)-3-pyrrolidinemethanamine as an oil. This material was used without further purification in the step.

N-Methyl-3-pyrrolidinemethanamine

A mixture of 67.3 g (0.32 mole) of N-methyl-1-(phenylmethyl)-3-pyrrolidinemethanamine, 3 g of 20% palladium on carbon, and 600 ml of methanol was shaken in an atmosphere of hydrogen at about $4.5 \times 10^5$ Pa and at room temperature for 18 hours. Another 3 g of 20% palladium on carbon was added and the hydrogenation continued for 6.5 hours. Another 3.0 g of 20% palladium on charcoal was added and the hydrogenation continued for another 4.5 hours. The catalyst was filtered and the filtrate evaporated under reduced pressure. The residue was distilled under vacuum (72–76° C, 10.5 mm Hg) to give 8.32 g N-methyl-3-pyrrolidinemethanamine.

Example D

N-Ethyl-3-pyrrolidinemethanamine

N-Ethyl-5-oxo-1-(phenylmethyl)-3-pyrrolidinecarboxamide

A mixture of 200 g (0.86 mole) of methyl-5-oxo-1-(phenylmethyl)pyrrolidinecarboxylate (J. Org. Chem., 26, 1519 (1961)], 1000 ml methanol and 200 g (4.4 mole) of ethylamine was heated at 100° C. in a pressure reactor for 17.2 hours. The reaction mixture was cooled and the excess ethylamine and methanol were removed under reduced pressure. The residue was taken up in dichloromethane and washed 3×150 ml 1N sodium hydroxide. The organic layer was dried over magnesium sulfate and the solvent removed at reduced pressure to give 104.6 g of N-ethyl-5-oxo-1-(phenylmethyl)-3-pyrrolidinecarboxamide as a white solid, mp 97–99° C.

This materials was used in the next step.

N-Ethyl-1-(phenylmethyl)-3-pyrrolidinemethanamine

To a suspension of 108.8 g (2.86 mole) lithium aluminum hydride in 800 ml tetrahydrofuran, was added a solution of 194.5 g (0.79 mole) of N-ethyl-5-oxo-1-(phenylmethyl)-3-pyrrolidinecarboxamide in 600 ml tetrahydrofuran dropwise under nitrogen. The reaction was then refluxed four hours. The reaction flask was cooled in an ice bath and 108 ml of water, 108 ml of 15% sodium hydroxide, and 324 ml of water were added. The precipitated solids were filtered and washed with hot ethanol. The combined filtrates were concentrated, then dissolved in dichloromethane, filtered, dried over magnesium sulfate, and the solvent evaporated under reduced pressure to give 151.9 g of N-ethyl-1-(phenylmethyl)-3-pyrrolidinemethanamine as an oil.

This material was used without further purification in the next step.

N-Ethyl-3-pyrrolidinemethanamine

A mixture of 151.6 g (0.69 mole) of N-ethyl-1-(phenylmethyl)-3-pyrrolidinemethanamine, 5 g of 20% palladium on carbon, and 1100 ml of ethanol was shaken in an atmosphere of hydrogen at about $4.5 \times 10^5$ Pa and at room temperature for 21.6 hours. Another 5 g of 20% palladium on carbon was added and the hydrogenation continued for 24 hours. The catalyst was filtered and the filtrate evaporated under reduced pressure. The residue was distilled under vacuum (88–91° C., 11.5 mm Hg) to give 66.0 g N-ethyl-3-pyrrolidinemethanamine.

Example E

N-(2,2,2-Trifluoroethyl)-3-pyrrolidinemethanamine

5-Oxo-1-(phenylmethyl)-N-(2,2,2-trifluoroethyl)-3-pyrrolidine carboxamide

A mixture of 21.9 g (0.10 mole) methyl 5-oxo-1-(phenylmethyl)-3-pyrrolidinecarboxylate in 150 ml tetrahydrofuran, was cooled to 0° C. in an ice bath under nitrogen and 24.3 g (0.15 mole) carbonyl diimidazole was added. The reaction was stirred at 0° C. for 30 minutes, then at room temperature for 30 minutes. A solution of 13.6 g (0.10 mole) of 2,2,2-trifluoroethylamine hydrochloride, 15.2 g (0.10 mole) 1,8-diazabicyclo[5.4.0]undec-7-ene and 100 ml tetrahydrofuran was added. The reaction was stirred at room temperature overnight. The solvent was removed at reduced pressure. The residue was taken up in dichloromethane and washed 3×150 ml saturated sodium bicarbonate. The organic layer was dried over magnesium sulfate and the solvent removed under reduced pressure. The product was purified by column chromatography on silica with ethyl acetate to give 8.50 g of 5-oxo-1-(phenylmethyl)-N-(2,2,2-trifluoroethyl)-3-pyrrolidinecarboxamide, mp 110–112° C.

This material was used in the next step.

1-(Phenylmethyl)-N-(2,2,2-trifluoroethyl)-3-pyrrolidinemethanamine

A mixture of 8.50 g (28.3 mole) of 5-oxo-1-(phenylmethyl)-N-(2,2,2-trifluoroethyl)-3-pyrrolidinecarboxamide in 100 ml tetrahydrofuran was added dropwise to 3.22 g (84.9 mmole) of lithium aluminum hydride in 50 ml tetrahydrofuran. The reaction was refluxed two hours, then stirred at room temperature overnight. The reaction was cooled in an ice bath and 3.2 ml of water, 3.2 ml of 15% sodium hydroxide, and 9.6 ml of water were added. The precipitated salts were filtered and washed with hot ethanol. The combined filtrates were concentrated under reduced pressure. The residue was taken up in dichloromethane, filtered, and dried over magnesium sulfate. The solvent was removed at reduced pressure to give 7.15 g of 1-(phenylmethyl)-N-(2,2,2-trifluoroethyl)-3-pyrrolidinemethanamine.

This material was used without further purification in the next step.

N-(2,2,2-Trifluoroethyl)-3-pyrrolidinemethanamine

A mixture of 7.15 g (26.3 mmole) 1-(phenylmethyl)-N-(2,2,2-trifluoroethyl)-3-pyrrolidinemethanamine 100 ml of methanol and 0.7 g of 20% palladium on carbon was shaken in an atmosphere of hydrogen at about $4.5 \times 10^5$ Pa and at room temperature for 24 hours. The catalyst was filtered and the filtrate evaporated under reduced pressure. The residue was distilled under vacuum (63–65° C., 2.8 mm Hg) to give 2.55 g of N-(2,2,2-trifluoroethyl)-3-pyrrolidinemethanamine.

Example F

N-Propyl-3-pyrrolidinemethanamine

5-Oxo-1-(phenylmethyl)-N-propyl-3-pyrrolidinecarboxamide

To a solution of 10.9 g (50 mmole) of 5-oxo-1-phenylmethyl)-3-pyrrolidinecarboxylic acid in 150 ml of acetonitrile was added 9.73 g (60 mmole) of 1,1'-carbonyldiimidazole. The reaction was heated to 60° C. for one hour, cooled to room temperature and treated with 4.13 g (70 mmole) of n-propylamine. After stirring for two hours, the solvent was removed in vacuo and the residue partitioned between ether and water. The organic layer was washed with water, 1N hydrochloric acid, dried over magnesium sulfate, filtered, and evaporated in vacuo to give 12.0 g of 5-oxo-1-(phenylmethyl)-N-propyl-3-pyrrolidinecarboxamide, mp 86–87° C.

1-(Phenylmethyl)-N-propyl-3-pyrrolidinemethanamine

To a suspension of 8.2 g (0.2 mole) of lithium aluminum hydride in 150 ml of dry tetrahydrofuran was added portionwise, 12.0 g (45.6 mmole) of solid 5-oxo-1-(phenylmethyl)-N-propyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 9.6 g of 1-(phenylmethyl)-N-propyl-3-pyrrolidinemethanamine, as a heavy syrup.

This material was used for the next step without further purification.

N-Propyl-3-pyrrolidinemethanamine

A mixture of 14.0 g (60.0 mmole) of 1-(phenylmethyl)-N-propyl-3-pyrrolidinemethanamine, 1.0 g of 20% palladium on carbon and 140 ml of methanol was shaken in an atmosphere of hydrogen at about $4.5 \times 10^5$ Pa and room temperature for 24 hours. The catalyst was removed by filtering through Celite, the filtrate concentrated and distilled in vacuo to give 7.1 g of N-propyl-3-pyrrolidinemethanamine, bp 49–50° C./0.25 mm.

Example G

N-Cyclopropyl-3-pyrrolidinemethanamine

5-Oxo-1-(phenylmethyl)-N-cyclopropyl-3-pyrrolidinecarboxamide

To a solution of 16.4 g (75 mmole) of 5-oxo-1-(phenylmethyl)-3-pyrrolidinecarboxylic acid in 150 ml of acetonitrile was added 13.8 g (85 mmole) of 1,1'-carbonyldiimidazole. The reaction was heated to 60° C. for one hour, cooled to room temperature and treated with 4.85 g (85 mmole) of cyclopropylamine. The reaction was stirred at room temperature for 18 hours, the solvent removed in vacuo and the residue partitioned between chloroform and water. The organic layer was washed with water, 1N hydrochloric acid, dried over magnesium sulfate, filtered, and evaporated in vacuo to give 18.3 g of 5-oxo-1-(phenylmethyl)-N-cyclopropyl-3-pyrrolidinecarboxamide, mp 94–96° C.

1-(Phenylmethyl)-N-cyclopropyl-3-pyrrolidine methanamine

To a suspension of 8.2 g (0.20 mole) of lithium aluminum hydride in 150 ml of dry tetrahydrofuran was added portionwise 18.0 g (70.0 mmole) of solid 5-oxo-1-(phenylmethyl)-N-cyclopropyl-3-pyrrolidinecarboxamide. When the addition was complete, the reaction mixture was stirred at room temperature for 18 hours and then at reflux for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 16.0 g of 1-(phenylmethyl)-N-cyclopropyl-3-pyrrolidinemethanamine, as a heavy oil. This was used for the next step without further purification.

N-Cyclopropyl-3-pyrrolidinemethanamine

A mixture of 13.6 g (59.0 mmol) of 1-(phenylmethyl)-N-cyclopropyl-3-pyrrolidinemethanamine, 0.5 g of 20% palladium on carbon and 140 ml of methanol was shaken in an atmosphere of hydrogen at about $4.5 \times 10^5$ Pa and room temperature for 24 hours. The catalyst was removed by filtering through Celite, the filtrate concentrated and distilled in vacuo to give 6.3 g of N-cyclopropyl-3-pyrrolidinemethanamine, bp 88–90°/13 mm.

Example H

N-(2-Propyl)-3-pyrrolidinemethanamine

5-Oxo-1-(phenylmethyl)-N-(2-propyl)-3-pyrrolidinecarboxamide

To a solution of 16.4 g (75.0 mmole) of 5-oxo-1-(phenylmethyl)-3-pyrrolidinecarboxylic acid in 150 ml of acetonitrile was added 13.8 g (85.0 mmole) of 1,1-'carbonyldiimidazole. The reaction was heated to 60° C. for one hour, cooled to room temperature and treated with 5.0 g (85 mmole) of isopropylamine. The reaction was stirred at room temperature for 18 hours, the solvent removed in vacuo and the residue partitioned between chloroform and water. The organic layer was washed with water, 1N hydrochloric acid, dried over magnesium sulfate, and evaporated in vacuo to give 18.6 g of 5-oxo-1-(phenylmethyl)-N-(2-propyl)-3-pyrrolidinecarboxamide, mp 122–124° C.

1-(Phenylmethyl)-N-(2-propyl)-3-pyrrolidinemethanamine

To a suspension of 8.2 g (0.2 mole) of lithium aluminum hydride in 150 ml of dry tetrahydrofuran was added portionwise, 18.3 g (70.0 mmole) of solid 5-oxo-1-phenylmethyl)-N-(2-propyl)-3-pyrrolidinecarboxamide. When the addition was complete, the reaction mixture was stirred at room temperature for 18 hours and then refluxed for two hours. After cooling to room temperature, the mixture was treated dropwise, successively, with 8 ml of water, 8 ml of 15% aqueous sodium hydroxide and 24 ml of water, titrating the final addition to produce a granular precipitate. The solid was removed by filtration, washed with tetrahydrofuran and the filtrate evaporated in vacuo to give 15.6 g of 1-(phenylmethyl)-N-(2-propyl)-3-pyrrolidinemethanamine as a heavy syrup.

This materials was used for the next step without further purification.

N-(2-Propyl)-3-pyrrolidinemethanamine

A mixture of 13.4 g (58.0 mmol) of 1-phenylmethyl-N-(2-propyl)-3-pyrrolidinemethanamine, 1.0 g of 20% palladium on carbon and 130 ml of methanol was shaken in an atmosphere of hydrogen at about $4.5 \times 10^5$ Pa and room temperature for 24 hours. The catalyst was removed by filtration through Celite; the filtrate concentrated and distilled in vacuo to give 6.3 g of N-(2-propyl)-3-pyrrolidinemethanamine, bp 58–60° C./3.5 mm.

Example I 1,1-Dimethylethyl(3-pyrrolidinyl)carbamate 1,1-Dimethylethyl[1-(phenylmethyl)-3-pyrrolidinyl]carbamate A solution of 77.0 g (0.44 mole) of 3-amino-1-(phenylmethyl)pyrrolidine [J. Med. Chem., 24, 1229 (1981)], 440 ml (0.44 mole) 1.0N sodium hydroxide and 600 ml of tertiarybutyl alcohol was treated dropwise with 98.2 g (0.45 mole) of di-tertiarybutyl dicarbomate. The reaction was stirred at room temperature for 18 hours and the solvent removed in vacuo. The residue was partitioned between ether and water. The aqueous layers were reextracted with ether, the combined ether layers were washed with water, dried (MgSO4), filtered, and evaporated on a steam bath replacing the ether with petroleum ether. The crystals which formed were removed by filtration, washed with ether/petroleum ether (1:1), and dried in vacuo to give 84.8 g of 1,1-dimethylethyl[1-(phenylmethyl)-3-pyrrolidinyl]carbamate, mp 114–115° C. A second crop (16.7 g) was obtained by concentrating the filtrate.

1,1-Dimethylethyl(3-pyrrolidinyl)carbamate

A mixture of 101.5 g (0.37 mole) of 1,1-dimethylethyl[1-(phenylmethyl)-3-pyrrolidinyl]carbamate, 5.0 g of 20% palladium on carbon and 1 liter of tetrahydrofuran was shaken in an atmosphere of hydrogen at about 50 psi and room temperature for 24 hours. The catalyst was removed by filtering through Celite, and the filtrate was concentrated in vacuo to give 6.8 g of 1,1-dimethylethyl (3-pyrrolidinyl)carbamate which solidified upon standing and was of sufficient purity to be used as is for the ensuing steps.

Example J

2-[(3-Pyrrolidinylmethyl)amino]ethanol

N-(2-Hydroxyethyl)-5-oxo-1-(phenylmethyl)-3-pyrrolidinecarboxamide

A mixture of 46.7 g (0.2 mole) of methyl 5-oxo-1-(phenylmethyl)-3-pyrrolidinecarboxylate [J. Org. Chem., 26, 1519 (1961)], 36.7 g (0.6 mole) of 2-aminoethanol and 500 ml methanol was refluxed overnight. The reaction was cooled to room temperature and the solvent removed at reduced pressure. The residue was taken up in dichloromethane and extracted 3×100 ml 1N sodium hydroxide. The aqueous layer was taken to pH 5, extracted 3×150 ml dichloromethane, then taken to pH 8 and again extracted 3×150 ml dichloromethane. The aqueous layer was concentrated at reduced pressure and the resulting slurry stirred in dichloromethane. The salts were filtered off. The combined organic layers were dried over magnesium sulfate, the solvent removed at reduced pressure to yield 47.9 g of N-(2-hydroxyethyl)-5-oxo-1-(phenylmethyl)-3-pyrrolidinecarboxamide as an oil. This was used in the next step without further purification.

2-[[[1-(Phenylmethyl)-3-pyrrolidinyl]methyl]amino]ethanol

A mixture of 46.6 g (0.18 mole) of N-(2-hydroxyethyl)-5-oxo-1-(phenylmethyl)-3-pyrrolidinecarboxamide in 200 ml of tetrahydrofuran was added dropwise to a slurry of 20.25 g (0.534 mole) of lithium aluminum hydride in 150 ml tetrahydrofuran. The reaction was refluxed three hours, then cooled in an ice bath. The work up consisted of sequential addition of 20 ml water, 20 ml 15% sodium hydroxide then 60 ml water. The reaction was filtered and the precipitate washed with ethanol. The filtrate was concentrated at reduced pressure, the residue taken up in dichloromethane, dried over magnesium sulfate, and the solvent removed at reduced pressure to give 32.31 g of 2-[[[1-(phenylmethyl)-3-pyrrolidinyl]methyl]amino]ethanol as an oil. This material was used in the next step without further purification.

2-[(3-Pyrrolidinylmethyl)amino]ethanol

A mixture of 32.3 g of 2-[[[1-(phenylmethyl)-3-pyrrolidinyl]methyl]amino]ethanol, 330 ml of methanol and 3 g of 20% palladium on charcoal was shaken in an atmosphere of hydrogen at about $4.5 \times 10^5$ Pa and at room temperature for 18 hours. The solvents were then removed at reduced pressure. The residue was distilled under vacuum (bp 129–131° C., 1.5 mm Hg) to give 11.43 g of 2-[(3-pyrrolidinylmethyl)amino]ethanol.

Example K

2-Methyl-2,7-diazaspiro[4.4]nonane Dihydrochloride

2-Methyl-2,7-diazaspiro[4.4]nonane-1,3,8-trione

A solution of 20.3 g (0.084 mole) 3-ethoxycarbonyl-5-oxo-3-pyrrolidineacetic acid, ethyl ester [J. Org. Chem., 46, 2757 (1981)] in 40 ml of 40% aqueous methylamine was stirred at room temperature overnight, then placed in an oil bath and gradually heated to 220° C. over 30 minutes allowing volatiles to distill from the open flask. The crude product was crystallized from ethanol to afford 12.6 g of 2-methyl-2,7-diazaspiro[4.4]nonane-1,3,8-trione, mp 201–204° C.

| Analysis calculated for C₈H₁₀N₂O₃: | | |
|---|---|---|
| C, 52.74; | H, 5.53; | N, 15.38 |
| Found C, 52.87; | H, 5.60; | N, 15.25. |

7-Benzyl-2-methyl-2,7-diazaspiro[4.4]nonane-1,3,8-trione

A solution of 1.82 g (10 mmol) of 2-methyl-2,7-diazaspiro[4.4]nonane-1,3,8-trione in 20 ml N,N-dimethylformamide was added gradually under a nitrogen atmosphere to 0.05 g (10.4 mmol) of 50% oil suspension of sodium hydride which had been previously washed twice with toluene and covered with 10 ml N,N-dimethylformamide. After stirring one hour there was added 1.40 g (11 mmol) of benzyl chloride and stirring was continued overnight at room temperature. After concentrating to a small volume in vacuo, the residue was diluted with 40 ml water and extracted twice with dichloromethane. The combined organic phase was washed with water, dried over magnesium sulfate, and evaporated to give a solid. Crystallization from toluene:hexane to afford 1.74 g of 7-benzyl-2-methyl-2,7-diazaspiro[4.4]nonane-1,3,8-trione, mp 157–158° C.

| Analysis calculated for C₁₅H₁₆N₂O₃: | | |
|---|---|---|
| C, 66.16; | H, 5.92; | N, 10.27 |
| Found C, 66.45; | H, 5.79; | N, 10.09. |

7-Phenylmethyl-2-methyl-2,7-diazaspiro[4.4]nonane Dihydrochloride

A solution of 1.36 g (5.0 mmol) 7-phenylmethyl-2-methyl-2,7-diazaspiro[4.4]nonane-1,3,8-trione in 50 ml tetrahydrofuran was added dropwise to a suspension of 0.95 g (25 mmol) lithium aluminum hydride in 30 ml tetrahydrofuran. The mixture was stirred overnight at room temperature, refluxed one hour, cooled, and treated dropwise with 0.95 ml water, 0.95 ml 15% sodium hydroxide solution, and 2.8 ml water. After removal of the inorganic solids by filtration, the filtrate was concentrated in vacuo to give a syrup which was dissolved in isopropanol and treated with excess 6N hydrogen chloride in isopropanol. Crystallization afforded 0.97 g of the title compound, mp 233–234° C.

| Analysis calculated for C₁₅H₂₄N₂Cl₂: | | | |
|---|---|---|---|
| C, 59.40; | H, 7.98; | N, 9.24; | Cl, 23.38 |
| Found C, 59.37; | H, 7.98; | N, 9.03; | Cl, 23.09. |

2-Methyl-2,7-diazaspiro[4.4]nonane Dihydrochloride

A solution of 7-benzyl-2-methyl-2,7-diazaspiro[4.4]nonane dihydrochloride in 150 ml of methanol with 1.0 g 20% palladium on carbon catalyst was hydrogenated at 4.5×10⁵ Pa for two days. After filtration, the filtrate was concentrated to a thick syrup which crystallized on addition of acetonitrile to give 11.5 g of 2-methyl-2,7-diazaspiro[4.4]nonane dihydrochloride, softened at 164° C. and melted at 168–170 ° C.

| Analysis calculated for C₈H₁₈N₂Cl₂: | | | |
|---|---|---|---|
| C, 45.08; | H, 8.51; | N, 13.15; | Cl, 33.27 |

| -continued Analysis calculated for C₈H₁₈N₂Cl₂: | | | |
|---|---|---|---|
| Found C, 45.24; | H, 8.77; | N, 13.18; | Cl, 33.26. |

Example L

2-Ethyl-2,7-diazaspiro[4.4]nonane Dihydrochloride

2-Ethyl-2,7-diazaspiro[4.4]nonane-1,3,8-trione

A suspension of 24.3 g (0.10 mmole) 3-ethoxycarbonyl-5-oxo-3-pyrrolidineacetic acid, ethyl ester in an excess of 2N sodium hydroxide, was stirred three hours at room temperature, acidified with dilute hydrochloric acid, and evaporated to dryness in vacuo. The product, 3-carboxy-5-oxo-3-pyrrolidineacetic acid, was taken up in isopropyl alcohol, separated from insoluble sodium chloride by filtration, concentrated to a syrup and dissolved in 100 ml 70% ethylamine. The solution was gradually heated in an oil bath up to 230° C. allowing volatiles to distill and then maintained at 230–240° C. for ten minutes. After cooling, the product was crystallized from isopropyl alcohol to afford 10.1 g of 2-ethyl-2,7-diazaspiro[4.4]nonane-1,3,8-trione, mp 168–169° C.

| Analysis calculated for C₉H₁₂N₂O₃: | | |
|---|---|---|
| C, 55.09; | H, 6.17; | N, 14.28 |
| Found C, 55.03; | H, 5.84; | N, 14.01. |

2-Ethyl-7-benzyl-2,7-diazaspiro[4.4]nonane-1,3,8-trione

A suspension of sodium hydride (2.20 g of 60% oil suspension (0.055 mole) washed with toluene) in 50 ml N,N-dimethylformamide was treated gradually with a solution of 10.0 g (0.051 mole) 2-ethyl-2,7-diazaspiro[4.4]nonane-1,3,8-trione in 100 ml N,N-dimethylformamide. After stirring 15 minutes, there was added dropwise 6.4 ml (0.055 mole) benzyl chloride and the mixture was stirred overnight, concentrated in vacuo and shaken with water-methylene chloride. The organic layers were dried, evaporated, and the product crystallized from toluene-hexane to afford 11.1 g of the title compound, mp 125–126.5° C.

| Analysis calculated for C₁₆H₁₈N₂O₃: | | |
|---|---|---|
| C, 67.11; | H, 6.34; | N, 9.79 |
| Found C, 67.41; | H, 6.33; | N, 9.79. |

2-Benzyl-7-ethyl-2,7-diazaspiro[4.4]nonane Dihydrochloride

A solution of 11.0 g (0.038 mole) 2-ethyl-7-benzyl-2,7-diazaspiro[4.4]nonane-1,3,8-trione in 100 ml tetrahydrofuran was added dropwise to a suspension of 6.00 g (0.158 mole) lithium aluminum hydride in 250 ml tetrahydrofuran. After stirring overnight, the mixture was refluxed one hour, cooled, and treated dropwise with 6 ml water, 6 ml 15% sodium hydroxide, and 18 ml water. Inorganic solids were separated by filtration and the filtrate was concentrated, taken up in ether, dried with magnesium sulfate, and reevaporated. The resulting syrup was dissolved in isopropyl alcohol and treated with excess hydrogen chloride in isopropyl alcohol to afford 9.63 g of the title compound, mp 196–198° C. (dec).

| Analysis calculated for $C_{16}H_{26}N_2Cl_2$: | | | |
| --- | --- | --- | --- |
| C, 60.56; | H, 8.26; | N, 8.83; | Cl, 22.35 |
| Found  C, 60.51; | H, 8.08; | N, 8.69; | Cl, 22.26. |

2-Ethyl-2,7-diazaspiro[4.4]nonane Dihydrochloride

A solution of 9.5 g (0.03 mole) 2-benzyl-7-ethyl-2,7-diazaspiro[4.4]nonane dihydrochloride in 100 ml methanol was hydrogenated with 1.0 g 20% palladium on carbon catalyst at $4.5 \times 10^5$ Pa for 22 hours. After filtration, the solution was concentrated to a syrup and crystallized from acetonitrile to afford 6.7 g of the title compound, mp 168–172° C.

| Analysis calculated for $C_9H_{20}N_2Cl_2$: | | | |
| --- | --- | --- | --- |
| C, 47.58; | H, 8.86; | N, 12.33; | Cl, 31.21 |
| Found  C, 47.70; | H, 8.58; | N, 12.39; | Cl, 30.92. |

Example M

1-Cyclopropyl-6,7,8-trifluoro-1,4-dihydro-4-oxo-3-quinolinecarboxylic Acid 2,3,4,5-Tetrafluorobenzoylacetic Acid, Ethyl Ester To 25.2 g (0.117 mol) of sodium 2,3,4,5-tetrafluorobenzoate, prepared as a dry powder from 2,3,4,5-tetrafluorobenzoic acid [J. Org. Chem., 29, 2381 (1961)] and aqueous sodium hydroxide with concentration to dryness, was added 400 ml of dry ether and the suspension was cooled to 0° C. Slowly, 25 ml ($\approx 2.5$ equivalents) of oxalyl chloride in 50 ml of ether was added and the mixture brought to room temperature where it was maintained for 2.0 hours. It was filtered and concentrated to remove low boiling impurities. The residue was dissolved in 100 ml of ether and placed in an addition funnel.

Meanwhile, 2.9 g (0.119 mol) of magnesium turnings were treated with 100 ml of absolute ethanol and 0.3 ml of carbon tetrachloride. To this mixture was added 18.6 ml (0.12 mol) of diethyl malonate in 75 ml of ether at a rate to keep the temperature just below reflux. When addition was complete, the reaction was refluxed for two hours. At $-20°$ C., the etheral acid chloride was slowly added. When addition was complete, the reaction was brought to 0° C. over 18 hours. The mixture was poured into dilute hydrochloric acid and was extracted into dichloromethane which was dried ($MgSO_4$) and concentrated. The residue was then treated with 340 mg of p-toluenesulfonic acid in 600 ml of water at 100° C. for two hours with rapid stirring. The oil was extracted into dichloromethane, dried ($MgSO_4$) and concentrated. The residue was purified by column chromatography (silica gel, using toluene:hexane:ether, 4:5:1), to give 18.5 g of a reddish oil. This material was triturated with pentane to give 10.2 g of 2,3,4,5-tetrafluorobenzoylacetic acid, ethyl ester, mp 49–51° C.

(2,3,4,5-Tetrafluorobenzoyl)-3-cyclopropylaminoacrylic Acid, Ethyl Ester

To 10.2 g (38.5 mmol) of the 2-(2,3,4,5-tetrafluorobenzoylacetic acid, ethyl ester was added 8.4 g (57.0 mmol) of triethylorthoformate and 9.3 g (91.5 mmol) of acetic anhydride. The mixture was heated to 150° C. for two hours and was then placed under high vacuum at 75–85° C. for one hour. The residue dissolved, without purification, in 100 ml of isopropyl alcohol and treated with 2.4 ml of cyclopropylamine. The reaction was allowed to stand overnight. It was concentrated and purified by column chromatography (silica gel 70–200, using hexane:chloroform:isopropyl alcohol, 80:15:5). The product off the column was recrystallized from pentane to give 6.16 g of 2-(2,3,4,5-tetrafluorobenzoyl)-3-cyclopropylaminoacrylic acid, ethyl ester, mp 63–64° C.

1-Cyclopropyl-6,7,8-trifluoro-1,4-dihydro-4-oxo-3-quinolinecarboxylic Acid

To 2.0 g (6.0 mmol) of the 2-(2,3,4,5-tetrafluorobenzoyl)-3-cyclopropylaminoacrylic acid, ethyl ester in 60 ml of dry dioxane was added 0.29 g of sodium hydride 50% dispersion) that was prewashed with pentane. The sodium hydride was delivered in 10 ml of dry tetrahydrofuran at 0° C. When evolution of hydrogen began to slow, the mixture was refluxed for two hours. It was concentrated, and the residue taken up in dichloromethane, which was water extracted, dried ($MgSO_4$), and concentrated. The residue was purified by column chromatography (silica gel 70–200 mesh, using chloroform:hexane:isopropanol, 4:5:1) to give 0.95 g of the 1-cyclopropyl-6,7,8-trifluoro-1,4-dihydro-4-oxo-3-quinolinecarboxylic acid, ethyl ester, mp 168–169° C. This material was dissolved in acetic acid at 100° C. and was treated with 10 ml of 0.5N hydrochloric acid for 2.5 hours. The mixture was cooled and water added. The solids were then collected to give 0.7 g of 1-cyclopropyl-1,4-dihydro-4-oxo-6,7,8-trifluoro-3-quinolinecarboxylic acid, mp 226–228° C.

Example N

7-Chloro-1-cyclopropyl-6-fluoro-1,4-dihydro-4-oxo-1,8-naphthyridine-3-carboxylic Acid 4-[6-(Cyclopropylamino)-3-nitro-2-pyridinyl]-1-piperazinecarboxylic Acid, Ethyl Ester A solution of 126.0 g (0.4 mole) of 4-(6-chloro-3-nitro-2-pyridinyl)-1-piperazinecarboxylic acid, ethyl ester (prepared as described in European Patent Publication No. 9425), 76.1 g (0.5 mole) of 1,8-diazabicyclo[5.4.0]undec-7-ene (DBU), 28.6 g (0.5 mole) of cyclopropylamine and 500 ml of absolute ethanol was stirred at room temperature for 48 hours. The solution was then heated at reflux for four hours and concentrated in vacuo. The residue was partitioned between chloroform and water. The chloroform layer was dried over magnesium sulfate and concentrated in vacuo. The residue was triturated with ether to give 64.0 g of the title compound, mp 100–103° C.

4-[6-(Acetylcyclopropylamino)-3-nitro-2-pyridinyl]-1-piperazinecarboxylic Acid, Ethyl Ester A solution of 64.0 g (0.19 mole) of 4-[6-(cyclopropylamino)-3-nitro-2-pyridinyl]-1-piperazinecarboxylic acid, ethyl ester, 115 ml of acetic anhydride and 115 ml of acetic acid was heated on a steam bath for 36 hours. The solvents were removed in vacuo, the residue was triturated with a mixture of ethanol and toluene which was also evaporated in vacuo to give 68.3 g of the title compound, mp 90–93° C.

4-[6-(Acetylcyclopropylamino)-3-amino-2-pyridinyl]-1-piperazinecarboxylic Acid, Ethyl Ester A mixture of 17.0 g (45 mmole) of 4-[6-(acetylcyclopropylamino)-3-nitro-2-pyridinyl-1-piperazine carboxylic acid, ethyl ester, 1.5 g of Raney nickel and 180 ml of absolute ethanol was shaken in an atmosphere of hydrogen at about 50 psi and room temperature for approximately 24 hours. The catalyst was removed by filtering through Celite and the solvent removed in vacuo to give 15.2 g of the title compound, mp 149–150° C.

2-[4-(Ethoxycarbonyl)-1-piperazinyl]-6-(acetylcyclopropylamino)-3-pyridinediazonium Tetrafluoroborate A solution of 20.8 g (60 mmole) of 4-(6-acetylcyclopropylamino)-3-amino-2-pyridinyl]-1-piperazine carboxylic acid, ethyl ester, 44 ml of ethanol and 27 ml of 48% tetrafluoroboric acid was cooled to 0° C. and treated dropwise with a solution of 4.56 g (66 mmol) of sodium nitrite in 8 ml of water under a nitrogen atmosphere keeping the temperature 0–5° C. After the addition was complete, the reaction was stirred at 0–5° C. for one hour and treated with 150 ml of anhydrous ether keeping the temperature below 10° C. The solid was removed by filtration, the precipitate was washed with ethanol/ether (1:1), ether and dried in vacuo to give 24.5 g of the title compound, mp 100–105° C. (dec).

4-[6-(Acetylcyclopropylamino)-3-fluoro-2-pyridinyl]-1-piperazinecarboxylic Acid, Ethyl Ester To 800 ml of refluxing toluene was added in portions, as a solid, 46.2 g (0.1 mole) of 2-[4-(ethoxycarbonyl)-1-piperazinyl]-6-acetylcyclopropylamino)-3-pyridinediazonium tetrafluoroborate. After the addition was complete, the reaction was refluxed for ten minutes and the toluene was decanted from the insoluble precipitate. The toluene was evaporated in vacuo, and the residue was partitioned between chloroform and water. The chloroform layer was washed with 5% aqueous sodium bicarbonate, water, dried over magnesium sulfate, and evaporated in vacuo to give 13.7 g of the title compound, as a viscous oil. An additional 10.2 g could be obtained by partitioning the original toluene insoluble material in chloroform and water. The organic layer was washed with 5% aqueous sodium bicarbonate, dried over magnesium sulfate, evaporated in vacuo and the residue was chromatographed on silica gel eluting with chloroform/ethyl acetate (6:4). This fraction was also a viscous oil which did not crystallize upon standing. Both fractions were of sufficient purity to be used as is in the ensuing steps.

4-[6-(Cyclopropylamino)-3-fluoro-2-pyridinyl]-1-piperazinecarboxylic Acid, Ethyl Ester A solution of 21.9 g (63 mmole) of 4-[6-(acetylcyclopropylamino)-3-fluoro-2-pyridinyl]-1-piperazinecarboxylic acid, ethyl ester, 170 ml of 15% hydrochloric acid and 235 ml of methanol was refluxed for one hour and allowed to stir at room temperature for 18 hours. The methanol was removed in vacuo and the aqueous acid was made basic with 1.0N sodium hydroxide to pH 10.5. The mixture was extracted with chloroform, the chloroform layer washed with water, dried over magnesium sulfate, and evaporated in vacuo to give 17.6 g of the title compound, mp 68–70° C.

1-Cyclopropyl-6-fluoro-1,4-dihydro-4-oxo-7-(1-piperazinyl)-1,8-naphthyridine-3-carboxylic Acid

Route A

[[Cyclopropyl[6-[4-(ethoxycarbonyl)-1-piperazinyl]-5-fluoro-2-pyridinyl]amino]methylene]propanedioic Acid, Diethyl Ester A solution of 3.8 g (12.3 mmole) of 4-[6-(cyclopropylamino)-3-fluoro-2-pyridinyl]-1-piperazine carboxylic acid, ethyl ester, 2.7 g (12.3 mmole) of diethyl(ethoxymethylene)malonate and 50 ml of xylene was refluxed for 24 hours. The solvent was removed in vacuo and the residue was chromatographed over silica gel eluting with chloroform/ethyl acetate (80/20) to give 2.3 g of the title compound as a viscous oil which was used without further purification.

Ethyl 1-Cyclopropyl-6-fluoro-1,4-dihydro-4-oxo-7-4-(ethoxycarbonyl)-1-piperazinyl]-1,8-naphthyridine-3-carboxylate A solution of 2.3 g (4.8 mmole) of [[cyclopropyl[6-[4-(ethoxycarbonyl)-1-piperazinyl]-5-fluoro-2-pyridinyl]amino]methylene]propanedioic acid, diethyl ester, in 15 ml of acetic anhydride was treated dropwise with 5 ml of 98% sulfuric acid keeping the temperature 55–60° C. When the addition was complete, the reaction was stirred for one hour and poured onto 50 g of ice. The aqueous suspension was extracted with chloroform, the chloroform layer washed with water, dried over magnesium sulfate, filtered, and evaporated in vacuo. The residue was triturated with several portions of ethanol/toluene which were also removed in vacuo to give 0.4 g of the title compound, mp 184–186° C. An additional 0.5 g of product could be obtained by concentrating the original aqueous fraction, mp 184–186° C.

1-Cyclopropyl-6-fluoro-1,4-dihydro-4-oxo-7-(1-piperazinyl)-1,8-naphthyridine-3-carboxylic Acid A suspension of 0.7 g (1.6 mmole) of ethyl 1-cyclopropyl-6-fluoro-1,4-dihydro-4-oxo-7-[4-(ethoxycarbonyl)-1-piperazinyl]-1,8-naphthyridine-3-carboxylate, 6 ml of 10% aqueous sodium hydroxide and 2 ml of ethanol was refluxed for three hours. The reaction was filtered through a fiber glass pad to clarify and acidified to pH 1.5 with 6.0M hydrochloric acid and lyophilized. The residue was dissolved in 10 ml of ammonium hydroxide and the solution concentrated in vacuo. The precipitate which formed was removed by filtration, washed with aqueous ethanol, ether, and dried in vacuo to give 0.04 g, mp 274–276° C.

Route B

4-[6-[Cyclopropyl(2,2-dimethyl-4,6-dioxo-1,3-dioxan 5-ylidine)amino]-3-fluoro-2-pyridinyl]-1-piperazinecarboxylic Acid, Ethyl Ester A solution of 17.6 g (57 mmole) of 4-[6-(cyclopropylamino)-3-fluoro-2-pyridinyl]-1-piperazine carboxylic acid, ethyl ester, 11.6 g (63 mmole) of 5-(methoxymethylene)-2,2-dimethyl-1,3-dioxane-4,6-dione and 250 ml of methanol was stirred at room temperature for four hours. The solid was removed by filtration, washed with methanol, ether and dried in vacuo to give 17.6 g of the title compound, mp 177–178° C.

1-Cyclopropyl-6-fluoro-1,4-dihydro-4-oxo-7-[4-(ethoxycarbonyl)-1-piperazinyl]-1,8-naphthyridine-3-carboxylic Acid A solution of 17.0 g (37.0 mmole) of 4-[6-(cyclopropyl-(2,2-dimethyl-4,6-dioxo-1,3-dioxan-5-ylidene)amino]-3-fluoro-2-pyridinyl]-1-piperazinecarboxylic acid, ethyl ester in 125 ml of acetic anhydride was treated dropwise with 35 ml of 98% sulfuric acid keeping the temperature 50–60° C. When the addition was complete, the reaction was stirred for two hours and poured onto 600 g of ice. The mixture was stirred for one hour and the resulting precipitate was removed by filtration, washed with water, and dried in vacuo to give 10.2 g of the title compound, mp 277–279° C.

1-Cyclopropyl-6-fluoro-1,4-dihydro-4-oxo-7-(1-piperazinyl-1,8-naphthyridine-3-carboxylic Acid A solution of 10.2 g (25 mmole) of 1-cyclopropyl-6-fluoro-1,4-dihydro-4-oxo-7-[4-(ethoxy carbonyl)-1-piperazinyl]-1,8-naphthyridine-3-carboxylic acid, 100 ml of 10% aqueous sodium hydroxide and 40 ml of ethanol was refluxed for three hours. The solution was concentrated to 125 ml and acidified to pH 7.3 with glacial acetic acid. The resulting precipitate was removed by filtration, washed with 50% aqueous ethanol, ether and dried in vacuo to give 7.2 g of the title compound, mp 274–276° C.

1-Cyclopropyl-6-fluoro-1,4-dihydro-7-hydroxy-4-oxo-1,8-naphthyridine-3-carboxylic Acid To a solution of 2 ml of 70% nitric acid in 10 ml of 98% sulfuric acid was added in portions 1.0 g (3.0 mmole) of 1-cyclopropyl-6-fluoro-1,4-dihydro-4-oxo-7-(1-piperazinyl)-1,8-naphthyridine-3carboxylic acid, keeping the temperature between 25–30° C. The resulting solution was stirred at room temperature for 18 hours and poured onto 40 g of ice. The mixture was stirred at room temperature for 24 hours, concentrated in vacuo, the pH adjusted to 12 with aqueous sodium hydroxide, and filtered through a fiber glass pad. The filtrate was acidified to pH 3.5 with 6.0M hydrochloric acid, the resulting precipitate removed by filtration, washed with water then ether and dried in vacuo to give 0.23 g of the title compound, mp 325–327° C.

7-Chloro-1-cyclopropyl-6-fluoro-1,4-dihydro-4-oxo-1,8-naphthyridine-3-carboxylic Acid A suspension of 0.19 g (0.72 mmole) of 1-cyclopropyl-6-fluoro-1,4-dihydro-7-hydroxy-4-oxo-1,8-naphthyridine-3-carboxylic acid in 2 ml of phosphorus oxychloride was heated at reflux for one-half hour. The resulting solution was cooled to room temperature and the solvent was removed in vacuo. The residue was triturated with ice water and the resulting solid was removed by filtration, washed with water, then ether, and dried in vacuo to give 0.11 g of the title compound, mp 209–212° C.

Example O

2-Nitro-3,4,5,6-tetrafluorobenzoyl Chloride

A solution of 6.7 g (28 mmoles) of 2-nitro-3,4,5,6-tetrafluorobenzoic acid [Tetrahedron, 23, 4719, (1967)], 3.8 g (30 mmoles) of oxalyl chloride and 50 ml of dichloromethane was treated with four drops of N,N-dimethylformamide and stirred at room temperature overnight. The solvent was removed and the residue was used as is without further purification.

Example P

2-Nitro-3,4,5,6-tetrafluoro-β-oxobenzenepropanoic Acid, Ethyl Ester

To a solution of 7.5 g (56.8 mmoles) of malonic half acid ester in 125 ml of dry tetrahydrofuran was added 20 mg of 2,2'-bipyridyl. The reaction mixture was cooled to −30° C. and treated dropwise with 24 ml (57.6 mmoles) of 2.4N n-butyl lithium. The reaction was then allowed to warm to −5° C. where a second equivalent, 24 ml (57.6 mmoles), of 2.4N n-butyl lithium was added until a light pink color persisted for 15 minutes. The reaction mixture was then cooled to −75° C. and treated dropwise with a solution of 7.2 g (28 mmoles) of 2-nitro-3,4,5,6-tetrafluorobenzoyl chloride in 15 ml of tetrahydrofuran. The reaction was stirred at −75° C. for one hour, warmed to −35° C., and quenched by pouring onto a solution of 28 ml of concentrated hydrochloric acid in 50 ml of ice water. The reaction was extracted with dichloromethane (3×200 ml), the organic layer was washed with 5% aqueous sodium bicarbonate (2×100 ml), and with 1.0M hydrochloric acid (1×100 ml), dried (MgSO4), and evaporated in vacuo to give 7.3 g of the title compound which was used for the ensuing step without further purification.

Example Q

Ethyl 1-Cyclopropyl-5-nitro-6,7,8-trifluoro-1,4-dihydro-4-oxo-3-quinolinecarboxylate A solution of 6.8 g (22 mmoles) of 2-nitro-3,4,5,6-tetrafluoro-β-oxobenzenepropanoic acid, ethyl ester, 4.9 g (33 mmoles) of triethylorthoformate and 50 ml of acetic anhydride was heated at reflux for two hours. The solvent was removed in vacuo and then in high vacuo at 80° C. for 1.5 hours. The residue was dissolved in 25 ml of t-butanol and treated with 1.43 g (25 mmoles) of cyclopropylamine. The mixture was heated at 45° C. for four hours, cooled to room temperature and treated dropwise with a solution of 2.47 g (25 mmoles) of potassium t-butoxide in 25 ml of t-butanol. The reaction was heated at 60° C. for six hours and the solvent was removed in vacuo. The residue was dissolved in chloroform, washed with water, dried (MgSO4), and evaporated in vacuo. The residue was chromatographed over silica gel eluting with chloroform/ethyl acetate (80/20) to give 1.9 g of the title compound as an oil which was used without further purification.

Example R

Ethyl 5-Amino-1-cyclopropyl-6,7,8-trifluoro-1,4-dihydro-4-oxo-3-quinolinecarboxylate A suspension of 1.9 g (5.3 mmoles) of ethyl 1-cyclopropyl-5-nitro-6,7,8-trifluoro-1,4-dihydro-4-oxo-3-quinolinecarboxylate, 0.5 g of Raney nickel and 100 ml of ethanol was shaken in a hydrogen atmosphere at pressures of 42.5–50 psi and temperatures of 24–26.5° C. for ten hours. The mixture was filtered through Celite and some insoluble product was dissolved in tetrahydrofuran with filtration. The combined filtrates were evaporated in vacuo and the residue was chromatographed on silica gel to give 600 mg of the title compound, mp 223–225° C.

Example S

5-Amino-1-cyclopropyl-6,7,8-trifluoro-1,4-dihydro-4-oxo-3-quinolinecarboxylic Acid A solution of 0.5 g (1.5 mmoles) of ethyl 5-amino-1-cyclopropyl-6,7,8-trifluoro-1,4-dihydro-4-oxo-3-quinolinecarboxylate, 5 ml of 6.0M hydrochloric acid and 5 ml of ethanol was heated at reflux for two hours. The solvent was removed in vacuo to give 430 mg of the title compound, mp 269-271° C.

Example T

3-Chloro-2,4,5-trifluoro-6-nitrobenzoic Acid

To a solution of 42.1 g (200 mmol) of 3-chloro-2,4,5-trifluorobenzoic acid (E.P.O. 0 183 129) in 100 ml of sulfuric acid was added concentrated nitric acid (50 ml) dropwise such that the reaction temperature stayed below 40° C. The reaction mixture was heated at 60° C. for 18 hours, then poured cautiously onto 500 g of ice water. The aqueous solution was extracted with ether, and the ether extracts were washed with water, dried over magnesium sulfate, and concentrated to give 26.5 g of 3-chloro-2,4,5-trilfuoro-6-nitrobenzoic acid.

Example U

3-Chloro-2,4,5-trifluoro-6-nitrobenzoyl Chloride

To a suspension of 25.6 g (100 mmol) of 3-chloro-2,4,5-trifluoro-6-nitrobenzoic acid in 75 ml of dichloromethane was added 14.0 g (110 mmol) of oxalyl chloride. This mixture was treated with four drops of dry N,N-dimethylformamide, and the rapidly bubbling solution was stirred overnight at room temperature. The mixture was concentrated to give 27.0 g of the title compound which was used without purification in the next step.

Example V

Ethyl (3-Chloro-2,4,5-trifluoro-6-nitro)-β-oxophenylpropanoate

To 26.4 g (200 mmol) of malonic half ethyl ester in 500 ml of dry tetrahydrofuran at −35° C. was added 91 ml of n-butyllithium (2.2M, 200 mmol) dropwise. A catalytic amount of bipyridyl (10 mg) was added, and the suspension was warmed to −5° C. Another equivalent of n-butyllithium (91 ml, 200 mmol) was added until the indicator turned pink. The mixture was cooled to −78° C., and a solution of 27 g of 3-chloro-2,4,5-trifluoro-6-nitrobenzoyl chloride in 50 ml of tetrahydrofuran was added dropwise. The reaction mixture was kept at −78° C. for one hour, then warmed to −35° C. and poured into a mixture of ice water (400 ml) and concentrated hydrochloric acid (17 ml). The solution was extracted with dichloromethane; the extracts were combined and washed with 5% sodium bicarbonate, 2M hydrochloric acid, and water. The dichloromethane was dried over magnesium sulfate and concentrated to give 27.4 g of the title compound.

Example W

Ethyl 2-(3-Chloro-2,4,5-trifluoro-6-nitrobenzoyl)-3-ethoxyacrylate

To 27.4 g (84.1 mmol) of the ethyl (3-chloro-2,4,5-trifluoro-6-nitro)-β-oxophenyl propanoate was added 18.7 g (126 mmol) of triethyl orthoformate and 100 ml of acetic anhydride. The mixture was refluxed for two hours, then cooled to 80° C., and concentrated to give 31.5 g of the title compound.

Example Y

Ethyl 8-Chloro-1-cyclopropyl-6,7-difluoro-1,4-dihydro-5-nitro-4-oxo-3-quinolinecarboxylate The ethyl 2-(3-chloro-2,4,5-trifluoro-6-nitrobenzoyl)-3-ethoxyacrylate prepared in the previous step was dissolved in 200 ml of t-butanol and treated with 5.0 g (88 mmol) of cyclopropylamine. The reaction mixture was warmed to 45° C. and stirred for three hours at that temperature. The solution was then cooled to room temperature and treated with a slurry of 9.4 g (84 mmol) of potassium t-butoxide in 50 ml of t-butanol. The mixture was stirred at 60° C. for five hours; the suspension was filtered, and the solid was washed with water and ether to give 21.7 g of the title compound.

Example Z

Ethyl 5-Amino-8-chloro-1-cyclopropyl-6,7-difluoro-1,4-dihydro-4-oxo-3-quinolinecarboxylate A suspension of 21.7 g (58.2 mmol) of ethyl 8-chloro-1-cyclopropyl-6,7-difluoro-1,4-dihydro-5-nitro-4-oxo-3-quinolinecarboxylate in 300 ml of ethanol and 300 ml of tetrahydrofuran was catalytically reduced using 3 g of Raney nickel in a hydrogen atmosphere of 50 psi. After twelve hours the mixture was diluted with dichloromethane and the catalyst was removed by filtration. The filtrate was concentrated to give 17.2 g of the title compound.

Example AA

5-Amino-8-chloro-1-cyclopropyl-6,7-difluoro-1,4-dihydro-4-oxo-3-quinolinecarboxylic Acid A suspension of 17.2 g (50.2 mmol) of ethyl 5-amino-8-chloro-1-cyclopropyl-6,7-difluoro-1,4-dihydro-4-oxo-3-quinolinecarboxylate in 100 ml of 6M hydrochloric acid was refluxed for three hours. The mixture was cooled to room temperature, and the solids were filtered, washed with water and ether, and dried to give 14.2 g of the title compound.

Using the same sequence of reactions the following compounds could be prepared:

5-amino-8-bromo-1-cyclopropyl-6,7-difluoro-1,4-dihydro-4-oxo-3-quinolinecarboxylic acid;

5-amino-1-cyclopropyl-6,7-difluoro-8-trifluoro-methyl-1,4-dihydro-4-oxo-3-quinolinecarboxylic acid;

5-amino-1-cyclopropyl-6,7-difluoro-1,4-dihydro-8-methoxy-4-oxo-3-quinolinecarboxylic acid;

5-amino-1-cyclopropyl-6,7-difluoro-1,4-dihydro-8-hydroxy-4-oxo-3-quinolinecarboxylic acid;

5,8-diamino-1-cyclopropyl-6,7-difluoro-1,4-dihydro-4-oxo-3-quinolinecarboxylic acid;

5-amino-1-cyclopropyl-6,7-difluoro-1,4-dihydro-4-oxo-3-quinolinecarboxylic acid; and 5-amino-7-chloro-1-cyclopropyl-6-fluoro-1,4-dihydro-4-oxo-1,8-naphthyridine-3-carboxylic acid.

Example BB

1-Cyclopropyl-6,7,8-trifluoro-1,4-dihydro-5-(methylamino)-4-oxo-3-quinolinecarboxylic Acid A solution of 5.9 g (20 mmol) of 5-amino-1-cyclopropyl-6,7,8-trifluoro-1,4-dihydro-4-oxo-3-quinolinecarboxylic acid, 20 ml of trifluoroacetic anhydride, and 100 ml of trifluoro acetic acid was stirred at room temperature overnight. The solution was evaporated to dryness and the residue was triturated with water and filtered to give 7.55 g of 1-cyclopropyl-6,7,8-trifluoro-1,4-dihydro-4-oxo-5-[(trifluoroacetyl)amino]-3-quinolinecarboxylic acid, mp 188° C.

A solution of 5.53 g (14.0 mmol) of the trifluoroacetyl intermediate above, 55 ml of DMF and 1.42 g (30.9 mmol) of 50% sodium hydride was stirred at 50–55° C. for 35 minutes. To this mixture was added 2.8 ml (45 mmol) of iodomethane with continued stirring at 50–55° C. for two hours and for three hours at room temperature. The reaction mixture was evaporated and the residue was triturated with water and filtered. The solid was dissolved with 60 ml of acetic acid and 30 ml of 6N HCl was added and the solution was heated under reflux for two hours. The solution was concentrated and the residual oil was treated with isopropanol to give 3.0 g of the title compound, mp 205–207° C.

In a similar manner, the following compounds were prepared: 8-chloro-1-cyclopropyl-6,7-difluoro-1,4-dihydro-5-(methylamino)-4-oxo-3-quinolinecarboxylic acid; 8-bromo-1-cyclopropyl-6,7-difluoro-1,4-dihydro-5-(methylamino)-4-oxo-3-quinolinecarboxylic acid; and 1-cyclopropyl-6,7-difluoro-8-trifluoromethyl-1,4-dihydro-5-(methylamino)-4-oxo-3-quinolinecarboxylic acid.

Example CC

1-Cyclopropyl-6,7,8-trifluoro-1,4-dihydro-5-dimethylamino-4-oxo-3-quinolinecarboxylic Acid 2-(Dimethylamino)-3,4,5,6-tetrafluorobenzoic Acid A solution of 10.0 g (41.8 mmol) of 2-nitro-3,4,5,6-tetrafluorobenzoic acid, 10 ml of 37% formaldehyde solution, 1.5 g of Raney nickel and 100 ml of ethanol was hydrogenated until TLC indicated absence of starting material. The reaction mixture was filtered and evaporated to an oil which was recrystallized with ethyl acetate-hexane to give 2.15 g of the title compound, mp 110–112° C. An additional 2.28 g, mp 90–100° C. was isolated from the filtrate.

2-(Dimethylamino)-3,4,5,6-tetrafluorobenzoyl Chloride

To a suspension of 4.22 g (17.8 mmol) of 2-(dimethylamino)-3,4,5,6-tetrafluorobenzoic acid and 85 ml of dichloromethane, added 1.7 ml (19.5 mmol) of oxalyl chloride. After the bubbling subsided, five drops of DMF were added and the solution was stirred at room temperature for 21 hours. The solution was evaporated to 4.8 g of an oil which was used in the next step without purification.

2-(Dimethylamino)-3,4,5,6-tetrafluoro-β-oxobenzenepropanoic Acid, Ethyl Ester

To a solution of 4.76 g (36 mmol) of malonic acid monoethyl ester and 75 ml of THF at −35° C. was added 25 ml (40 mmol) of 1.5N n-butyl lithium solution. The remaining 25 ml (40 mmol) of 1.5N butyllithium solution was added at 0°. After cooling to −78° C., a solution of the 4.8 g of 2-(dimethylamino)-3,4,5,6-tetrafluorobenzoyl chloride in 50 ml of THF was added to the dilithio malonate over a 15 minute period. The reaction mixture was stirred for 1.75 hours while the temperature came up to −30° C. The reaction mixture was poured into ice, water, and 50 ml of 1N HCl. The mixture was extracted with ether and the ether extract was washed with H$_2$O, 5% NaHCO$_3$, and HCl. After drying over MgSO$_4$ the ether solution was concentrated to 4.4 g of oil product. NMR spectra indicated the desired product.

2-(Dimethylamino)-α-(ethoxymethylene)-3,4,5,6-tetrafluoro-β-oxobenzenepropanoic Acid, Ethyl Ester A solution of 4.4 g (14.3 mmol) of the crude ketoester, 3.57 ml (21.5 mmol) of triethylortho formate, and 25 ml of acetic anhydride was heated under reflux for two hours. The solution was evaporated to 5.2 g of oil which was used in the next step without purification.

α-[(Cyclopropylamino)methylene]-2-(dimethylamino)-3,4,5,6-tetrafluoro-β-oxobenzenepropanoic Acid, Ethyl Ester To a solution of 5.2 g (14.3 mmol) of the above crude product in 50 ml of t-butanol was added 1.2 ml (17 mmol) of cyclopropylamine. The reaction solution was stirred for 18 hours at room temperature. The reaction mixture was filtered to give 0.12 g of the title compound, mp 122–124° C. TLC of the filtrate showed it to be the same as the solid.

5-(Dimethylamino)-1-cyclopropyl-6,7,8-trifluoro-1,4-dihydro-4-oxo-3-quinolinecarboxylic Acid To the above filtrate was added 1.7 g (15 mmol) of potassium t-butoxide and the mixture was stirred at room temperature for 1.5 hours. TLC showed no change in reactants. An additional 1.7 g (15 mmol) of potassium t-butoxide was added and the reaction mixture was heated at 50–55° C. for two hours. After TLC indicated the reaction was complete, the solution was evaporated to 4 g of an oil. This oil was heated with 100 l 6N HCl for three hours on the steam bath. The solution was evaporated and the residue was recrystallized from isopropanol to give 0.3 g of the title compound, mp 160–163° C. An additional 1.0 g of solid was added from the filtrate.

Following the same sequence, the following compounds were prepared: 8-chloro-1-cyclopropyl-6,7difluoro-1,4-dihydro-5-dimethylamino-4-oxo-3-quinolinecarboxylic acid, and 8-bromo-1-cyclopropyl-6,7-difluoro-1,4-dihydro-5-dimethylamino-4-oxo-3-quinolinecarboxylic acid.

Example DD

1-Cyclopropyl-6,7,8-trifluoro-1,4-dihydro-5-methoxy-4-oxo-3-quinolinecarboxylic Acid To 22.4 g (100 mmol) of the 2-methoxy-3,4,5,6-tetrafluorobenzoic acid prepared as in [J. Fluorine Chem., 28, 361 (1985)] was added 400 ml of tetrahydrofuran, 1 ml of dimethylformamide, and 13 ml of oxalylchloride. The acid chloride mixture was concentrated, diluted with 100 ml of tetrahydrofuran, and added to a solution of the dilithio anion of malonic acid monoethylester (200 mmol) in 800 ml of tetrahydrofuran at −70° C. The reaction was stirred for one hour at −30° C., poured over ice and dilute hydrochloric acid and taken into dichloromethane. The product was isolated by an extraction at pH 7, followed by drying the dichloromethane (MgSO$_4$) and concentration. The crude product was then treated neat with 2.5 equivalents of triethylorthoformate and 2.8 equivalents of acetic anhydride at 150° C. for two hours. The mixture was concentrated and at room temperature a slight excess of cyclopropylamine (6.0 g) was added in 150 ml of t-butanol. The mixture was stirred overnight. To this mixture was added 11.3 g of potassium t-butoxide and the temperature brought to 50° C. The mixture was concentrated after 18 hours and the residue treated with 100 ml of acetic acid and 100 ml of 4N hydrochloric acid. From this mixture after four hours at 100° C., 12.7 g of the title compound precipitated.

In a similar manner, the following compounds were prepared: 8-chloro-1-cyclopropyl-6,7-difluoro-1,4-dihydro-5-methoxy-4-oxo-3-quinolinecarboxylic acid; 8-bromo-1-cyclopropyl-6,7-difluoro-1,4-dihydro-5-methoxy-4-oxo-3-quinolinecarboxylic acid; 1-cyclopropyl-6,7-difluoro-8-trifluoromethyl-5-methoxy-4-oxo-3-quinolinecarboxylic acid; and 1-cyclopropyl-6,7-difluoro-1,4-dihydro-5-methoxy-4-oxo-3-quinolinecarboxylic acid.

Example EE

1-Cyclopropyl-6,7,8-trifluoro-1,4-dihydro-5-hydroxy-4-oxo-3-quinolinecarboxylic Acid To 1.5 g of 1-cyclopropyl-6,7,8-trifluoro-1,4-dihydro-5-methoxy-4-oxo-3-quinolinecarboxylic acid was added 25 ml of hydrogen bromide in acetic acid (32%). The mixture was stirred at room temperature for 16 hours and concentrated to dryness. The residue was triturated with water:ethanol and filtered to give 1.15 g of the title compound.

In a similar manner the following compounds were prepared: 8-chloro-1-cyclopropyl-6,7-difluoro-1,4-dihydro-5-hydroxy-4-oxo-3-quinolinecarboxylic acid; 8-bromo-1-cyclopropyl-6,7-difluoro-1,4-dihydro-5-hydroxy-4-oxo-3-quinolinecarboxylic acid; 1-cyclopropyl-6,7-difluoro-8-trifluoromethyl-5-hydroxy-4-oxo-3-quinolinecarboxylic acid and 1-cyclopropyl-6,7-difluoro-1,4-dihydro-5-hydroxy-4-oxo-3-quinolinecarboxylic acid.

Example 1

1-Ethyl-5-amino-6,8-difluoro-7-[3-(t-butoxycarbonylamino)-1-pyrrolidinyl]-4-oxo-1,4-dihydroquinoline-3-carboxylic Acid A suspension of 3.02 g (10 mmole) of 1-ethyl-5-amino-6,7,8-trifluoro-4-oxo-1,4-dihydro quinoline-3-carboxylic acid, 2.79 g (15 mmole) of 3-(t-butoxycarbonylamino)pyrrolidine, 3.0 g (30 mmole) of triethylamine and 100 ml of acetonitrile is refluxed for 18 hours. The reaction mixture is cooled to room temperature and the precipitate is removed by filtration, washed with acetonitrile, ether, and dried in vacuo to give 1-ethyl-5-amino-6,8-difluoro-7-[3-(t-butoxycarbonylamino)-1-pyrrolidinyl]-4-oxo-1,4-dihydroquinoline-3-carboxylic acid.

Example 2

1-Ethyl-5-amino-6,8-difluoro-7-(3-amino-1-pyrrolidinyl)-4-oxo-1,4-dihydroquinoline-3-carboxylic Acid Hydrochloride A near solution of 4.5 g (10 mmole) of 1-ethyl-5-amino-6,8-difluoro-7-[3-(t-butoxycarbonylamino)-1-pyrrolidinyl]-4-oxo-1,4-dihydroquinoline-3-carboxylic acid, 10 ml of 6.0M hydrochloric acid and 100 ml of glacial acetic acid is heated at 60° C. for four hours and then stirred at room temperature for 18 hours. The solvent is removed in vacuo, the residue triturated with ethanol/ether (1:1), filtered, washed with ether, and dried in vacuo to give the title compound.

Example 3

1-Ethyl-5-amino-6,8-difluoro-7-[3-(ethylamino)methyl-1-pyrrolidinyl)]-4-oxo-1,4-dihydroquinoline-3-carboxylic Acid A suspension of 3.02 g (10 mmole) of 1-ethyl-5-amino-6,7,8-trifluoro-4-oxo-1,4-dihydro quinoline-3-carboxylic acid, 1.93 g (15 mmole) of N-ethyl-3-pyrrolidinemethanamine, 3.0 g (30 mmole) of triethylamine and 100 ml of acetonitrile is refluxed for 18 hours. The reaction mixture is cooled to room temperature and the precipitate is removed by filtration, washed with acetonitrile, ether, and dried in vacuo to give 1-ethyl-5-amino-6,8-difluoro-7-[3-(ethylamino)methyl-1-pyrrolidinyl)]-4-oxo-1,4-dihydroquinoline-3-carboxylic acid.

The following compounds may be prepared from 1-ethyl-5-amino-6,7,8-trifluoro-4-oxo-1,4-dihydroquinoline-3-carboxylic acid and the desired amine or protected amine using the method above: 1-ethyl-5-amino-6,8-difluoro-7-[3-(aminomethyl)-1-pyrrolidinyl]-4-oxo-1,4-dihydroquinoline-3-carboxylic acid; 1-ethyl-5-amino-6,8-difluoro-7-[3-(propylaminomethyl)-1-pyrrolidinyl]-4-oxo-1,4-dihydroquinoline-3-carboxylic acid; 1-ethyl-5-amino-6,8-difluoro-7-[3-(2-propylaminomethyl)-1-pyrrolidinyl]-4-oxo-1,4-dihydroquinoline-3-carboxylic acid; 1-ethyl-5-amino-6,8-difluoro-7-[3-(cyclopropylaminomethyl)-1pyrrolidinyl]-4-oxo-1,4-dihydroquinoline-3-carboxylic acid; 1-ethyl-5-amino-6,8-difluoro-7-[2,7-diazaspiro[4.4]non-2-yl]-4-oxo-1,4-dihydroquinoline-3-carboxylic acid; 1-ethyl-5-amino-6,8-difluoro-7-[7-methyl-2,7-diazaspiro[4.4]non-2-yl]-4-oxo-1,4-dihydroquinoline-3-carboxylic acid; 1-ethyl-5-amino-6,8-difluoro-7-[7-ethyl-2,7-diazaspiro[4.4]non-2-yl]-4-oxo-1,4-dihydroquinoline-3-carboxylic acid; 1-ethyl-5-amino-6,8-difluoro-7-[3-[[(2-hydroxyethyl)amino]methyl]-1-pyrrolidinyl]-4-oxo-1,4-dihydroquinoline-3-carboxylic acid; and 1-ethyl-5-amino-6,8-difluoro-7-[3-[[(2,2,2-trifluoroethyl)amino]methyl]-1-pyrrolidinyl]-4-oxo-1,4-dihydroquinoline-3-carboxylic acid.

Example 4

8-Amino-9-fluoro-3-methyl-10-[(3-t-butoxycarbonylamino)-1-pyrrolidinyl]-7-oxo-2,3-dihydro-7H-pyrido [1,2,3-de][1,4]benzoxazine-6-carboxylic Acid A solution of 2.9 g (10 mmole) of 8-amino-9,10-difluoro-3-methyl-7-oxo-2,3-dihydro-7H-pyrido [1,2,3-de][1,4]benzoxazine-6-carboxylic acid, 2.8 g (15 mmole) of 3-(t-butoxycarbonylamino)pyrrolidine, 3.03 g (30 mmole) of triethylamine and 100 ml of N,N-dimethylformamide is heated at 100° C. for four hours. The solvent is removed in vacuo and the residue is triturated with water. The aqueous slurry is adjusted to pH 7.2 with 1.0M hydrochloric acid and the precipitate is removed by filtration, washed with water, and dried in vacuo to give the 8-amino-9-fluoro-3-methyl-10-[(3-t-butoxycarbonylamino)-1-pyrrolidinyl]-7-oxo-2,3-dihydro-7H-pyrido[1,2,3-de][1,4]benzoxazine-6-carboxylic acid.

Example 5

8-Amino-9-fluoro-3-methyl-10-(3-amino-1-pyrrolidinyl)-7-oxo-2,3-dihydro-7H-pyrido[1,2,3-de][1,4-]benzoxazine-6-carboxylic Acid, Hydrochloride A suspension of 4.63 g (10.0 mmole) of 8-amino-9-fluoro-3-methyl-10-[(3-t-butoxycarbonyl amino)-1-pyrrolidinyl]-7-oxo-2,3-dihydro-7H-pyrido [1,2,3-de][1,4-]benzoxazine-6-carboxylic acid 5 ml of 6.0M hydrochloric acid and 50 ml of glacial acetic acid is heated at 60° C. for four hours. The solvent is removed in vacuo and the residue is triturated with ethanol/ether (1:1). The precipitate is removed by filtration, washed with ether, and dried in vacuo to give 8-amino-9-fluoro-3-methyl-10-(3-amino-1-pyrrolidinyl)-7-oxo-2,3-dihydro-7H-pyrido[1,2,3-de][1,4]benzoxazine-6-carboxylic acid, hydrochloride.

Example 6

8-Amino-9-fluoro-3-methyl-10-[(3-cyclopropylaminomethyl)-1-pyrrolidinyl]-7-oxo-2,3-dihydro-7H-pyrido [1,2,3-de][1,4]benzoxazine-6-carboxylic Acid A mixture of 2.96 g (10 mmole) of 8-amino-9,10-difluoro-3-methyl-7-oxo-2,3-dihydro-7H-pyrido [1,2,3-de][1,4]benzoxazine-6-carboxylic acid, 2.1 g (15 mmole) of N-cyclopropyl-3-pyrrolidinemethanamine, 3.03 g (30 mmole) of triethylamine and 100 ml of N,N-dimethylformamide is heated at. 100° C. for four hours. The solvent is removed in vacuo and the residue triturated with water. The aqueous suspension is adjusted to pH 7.2 with 1.0M hydrochloric acid. The solid is removed by filtration, washed with water, and dried in vacuo to give 8-amino-9-fluoro-3-methyl-10-[(3-cyclopropylaminomethyl)-1-pyrrolidinyl]-7-oxo-2,3-dihydro-7H-pyrido[1,2,3-de][1,4]benzoxazine-6-carboxylic acid.

The following compounds may be prepared from 8-amino-9,10-difluoro-3-methyl-7-oxo-2,3-dihydro-7H-pyrido[1,2,3-de][1,4]benzoxazine-6-carboxylic acid and the desired amine or protected amine using the above method: 8-amino-9-fluoro-3-methyl-10-[3-(aminomethyl)-1-pyrrolidinyl]-7-oxo-2,3-dihydro-7H-pyrido[1,2,3-de][1,4]benzoxazine-6-carboxylic acid; 8-amino-9-fluoro-3-methyl-10-[3-[(propylamino)methyl)-1-pyrrolidinyl]-7-oxo-2,3-dihydro-7H-pyrido [1,2,3-de][1,4]benzoxazine-6-carboxylic acid; 8-amino-9-fluoro-3-methyl-10-[3-[(2-hydroxyethyl)amino)methyl]-1-pyrrolidinyl]-7-oxo-2,3-dihydro-7H-pyrido[1,2,3-de][1,4]benzoxazine-6-carboxylic acid; 8-amino-9-fluoro-3-methyl-10-[3-[(2-propylamino)methyl]-1-pyrrolidinyl]-7-oxo-2,3-dihydro-7H-pyrido[1,2,3-de][1,4-]benzoxazine-6-carboxylic acid; 8-amino-9-fluoro-3-methyl-10-[3-[(2,2,2-trifluoroethyl)amino]methyl]-1-pyrrolidinyl]-7-oxo-2,3-dihydro-7H-pyrido[1,2,3-de][1,4]benzoxazine-6-carboxylic acid; 8-amino-9-fluoro-3-methyl-10-[3-[(ethylamino)methyl]-1-pyrrolidinyl]-7-oxo-2,3-dihydro-7H-pyrido[1,2,3-de][1,4-]benzoxazine-6-carboxylic acid; 8-amino-9-fluoro-3-methyl-10-[2,7-diazaspiro[4.4]non-2-yl]-7-oxo-2,3-dihydro-7H-pyrido [1,2,3-de][1,4]benzoxazine-6-carboxylic acid; 8-amino-9-fluoro-3-methyl-10-[7-(7-methyl)-2,7-diazaspiro[4.4]non-2-yl]-7-oxo-2,3-dihydro-7H-pyrido [1,2,3-de][1,4]benzoxazine-6-carboxylic acid; and 8-amino-9-fluoro-3-methyl-10-[7-(7-ethyl)-2,7-diazaspiro[4.4]non-2-yl]-7-oxo-2,3-dihydro-7H-pyrido [1,2,3-de][1,4]benzoxazine-6-carboxylic acid.

Example 7

5-Amino-1-cyclopropyl-6,8-difluoro-7-[(3-ethylaminomethyl)-1-pyrrolidinyl]-1,4-dihydro-4-oxo-3-quinolinecarboxylic Acid A solution of 0.43 g (1.5 mmoles) of 5-amino-1-cyclopropyl-6,7,8-trifluoro-1,4-dihydro-4-oxo-3-quinolinecarboxylic acid, 0.61 g (6.0 mmoles) of triethylamine, 0.77 g (6.0 mmoles) 3-(ethylaminomethyl)pyrrolidine and 25 ml of acetonitrile was heated at reflux for two hours. The solvent was removed in vacuo and the residue was dissolved in water and filtered through a fiber glass pad to remove a trace of insoluble material. The filtrate was adjusted to pH 7.0 and the resulting precipitate removed by filtration, washed with water, and dried in vacuo to give 200 mg of the title compound, mp 250–252° C.

Example 8

5-Amino-7-(3-amino-1-pyrrolidinyl)-8-chloro-1-cyclopropyl-6-fluoro-1,4-dihydro-4-oxo-3-quinolinecarboxylic Acid To 1.57 g (5 mmol) of 5-amino-8-chloro-1-cyclopropyl-6,7-difluoro-1,4-dihydro-4-oxo-3-quinoline carboxylic acid in 20 ml of acetonitrile was added 0.93 g (5 mmol) of 3-[(t-butoxycarbonyl)amino]pyrrolidine and 1.0 g (10 mmol) of triethylamine. The mixture was refluxed for three hours, cooled, and filtered. The solids were washed with acetonitrile and ether, then dissolved in 10 ml of acetic acid and 2 ml of 3N hydrochloric acid. The mixture was heated at 100° C. for four hours, concentrated, and triturated with 2-propanol. The solid that formed was filtered and washed with ether to give 1.2 g of the title compound.

The following compounds were also prepared by a similar procedure: 5-amino-8-chloro-1-cyclopropyl-7-[3-[(ethylamino)methyl]-1-pyrrolidinyl]-6-fluoro-1,4-dihydro-4-oxo-3-quinolinecarboxylic acid; 5-amino-8-chloro-1-cyclopropyl-6-fluoro-1,4-dihydro-7-[3-[(methylamino)methyl]-1-pyrrolidinyl]-4-oxo-3quinolinecarboxylic acid; 5-amino-8-chloro-1-cyclopropyl-6-fluoro-1,4-dihydro-7-[3-[(dimethylamino) methyl]-1-pyrrolidinyl]-4-oxo-3-quinolinecarboxylic acid; 5-amino-7-[3-(aminomethyl)-3-methyl-1-pyrrolidinyl]-8-chloro-1-cyclopropyl-6-fluoro-1,4-dihydro-4-oxo-3-quinolinecarboxylic acid; 5-amino-8-bromo-1-cyclopropyl-7-[3-[(ethylamino)methyl]-1-pyrrolidinyl]-6-fluoro-1,4-dihydro-4-oxo-3-quinolinecarboxylic acid; 5-amino-8-bromo-1-cyclopropyl-6-fluoro-1,4-dihydro-7-[3-[(methylamino)methyl]-1-pyrrolidinyl]-4-oxo-3-quinolinecarboxylic acid; 5-amino-8-bromo-1-cyclopropyl-6-fluoro-1,4-dihydro-7-[3-[(dimethylamino)methyl]-1-pyrrolidinyl]-4-oxo-3-quinolinecarboxylic acid; 5-amino-7-(3-amino-1-pyrrolidinyl)-8-bromo-1-cyclopropyl-6-fluoro-1,4-dihydro-4-oxo-3-quinolinecarboxylic acid; 5-amino-7-(3-amino-1-pyrrolidinyl)-1-cyclopropyl-6-fluoro-8-trifluoromethyl-1,4-dihydro-4-oxo-3-quinolinecarboxylic acid; 5-amino-1-cyclopropyl-6-fluoro-8-trifluoromethyl-1,4-dihydro-7-[3-[(methylamino) methyl]-1-pyrrolidinyl]-4-oxo-3-quinolinecarboxylic acid; 5-amino-1-cyclopropyl-7-[3-[(ethylamino) methyl]-1-pyrrolidinyl]-6-fluoro-8-trifluoromethyl-4-oxo-3-quinolinecarboxylic acid; 5-amino-1-cyclopropyl-6-fluoro-8-trifluoromethyl-1,4-dihydro-7-[3-[(dimethylamino)methyl]-1-pyrrolidinyl]-4-oxo-3-quinolinecarboxylic acid; 5-amino-1-cyclopropyl-7-[3-[(ethylamino)methyl]-1-pyrrolidinyl]-6-fluoro- 1,4-dihydro-8-methoxy-4-oxo-3-quinolinecarboxylic acid; 5-amino-1-cyclopropyl-6-fluoro-1,4-dihydro-7-[3-[(methylamino)methyl]-1-pyrrolidinyl]-8-methoxy-4-oxo-3-quinolinecarboxylic acid; 5-amino-1-cyclopropyl-6-fluoro-1,4-dihydro-7-[3-[(dimethylamino)methyl]-1-pyrrolidinyl]-8-methoxy-4-oxo-3quinolinecarboxylic acid; 5-amino-7-(3-amino-1-pyrrolidinyl)-1-cyclopropyl-6-fluoro-1,4-dihydro-8-methoxy-4-oxo-3-quinolinecarboxylic acid; 5-amino-1-cyclopropyl-7-[3-[(ethylamino)methyl]-1-pyrrolidinyl]-6-fluoro-1,4-dihydro-8-hydroxy-4-oxo-3-quinolinecarboxylic acid; 5-amino-1-cyclopropyl-6-fluoro-1,4-dihydro-8-hydroxy-7-[3-[(methylamino) methyl]-1-pyrrolidinyl]-4-oxo-3-quinolinecarboxylic acid; 5-amino-1-cyclopropyl-6-fluoro-1,4-dihydro-8-hydroxy-7-[3-[(dimethylamino)methyl]-1-pyrrolidinyl]-4-oxo-3-quinolinecarboxylic acid; 5-amino-7-(3-amino-1-pyrrolidinyl)-1-cyclopropyl-6-fluoro-1,4-dihydro-8-hydroxy-4-oxo-3-quinolinecarboxylic acid; 7-(3-amino-1-pyrrolidinyl)-8-chloro-1-cyclopropyl-6-fluoro-1,4-dihydro-5-methoxy-4-oxo-3-quinolinecarboxylic acid; 7-(3-amino-1-pyrrolidinyl)-8-chloro-1-cyclopropyl-6-fluoro-1,4-dihydro-5-hydroxy-4-oxo-3quinolinecarboxylic acid; 7-(3-amino-1-pyrrolidinyl)-8-chloro-1-cyclopropyl-6-fluoro-1,4-dihydro-5-methylamino-4-oxo-3-quinolinecarboxylic acid; 7-(3-amino-1-pyrrolidinyl)-8-chloro-1-cyclopropyl-6-fluoro-1,4-dihydro-5-dimethylamino-4-oxo-3-quinolinecarboxylic acid; 8-chloro-1-cyclopropyl-7-[3-[(dimethylamino) methyl]-1-pyrrolidinyl]-6-fluoro-1,4-dihydro-5-methoxy-4-oxo-3-quinolinecarboxylic acid; 8-chloro-1-cyclopropyl-7-[3-[(dimethylamino)methyl]-1-pyrrolidinyl]-6-fluoro-1,4-dihydro-5-hydroxy-4-oxo-3-quinolinecarboxylic acid.

We claim:

1. A compound of the formula

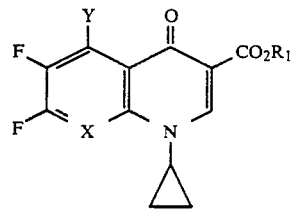

wherein X is CH, N, CF, CCl, CBr, COH, or COR; Y is $NH_2$, NHR, NRR', OR, or OH wherein R and R' are each independently an alkyl of from one to six carbon atoms or a cycloalkyl of from three to six carbon atoms; $R_1$ is hydrogen, alkyl having from one to six carbon atoms, or a cation and the pharmaceutically acceptable acid addition or base salts thereof.

2. A compound according to claim 1 wherein X is CCl, CBr or CF and Y is $NH_2$, NHR or NRR'.

3. A compound as claimed in claim 1 and being 5-amino-8-chloro-1-cyclopropyl-6,7-difluoro-1,4-dihydro-4-oxo-3-quinolinecarboxylic acid.

4. A compound as claimed in claim 1 and being 5-amino-8-bromo-1-cyclopropyl-6,7-difluoro-1,4-dihydro-4-oxo-3-quinolinecarboxylic acid.

5. A compound as claimed in claim 1 and being 5-amino-1-cyclopropyl-6,7,8-trifluoro-1,4-dihydro-4-oxo-3-quinolinecarboxylic acid.

* * * * *